(12) United States Patent
Altaf et al.

(10) Patent No.: US 9,573,967 B2
(45) Date of Patent: Feb. 21, 2017

(54) N-HETEROCYCLIC CARBENE GOLD COMPLEXES WITH ANTICANCER PROPERTIES AND METHODS OF USE THEREOF

(71) Applicant: KING FAHD UNIVERSITY OF PETROLEUM AND MINERALS, Dhahran (SA)

(72) Inventors: Muhammad Altaf, Dhahran (SA); Anvarhusein Abdulkadir Isab, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 79 days.

(21) Appl. No.: 14/705,627

(22) Filed: May 6, 2015

(65) Prior Publication Data
US 2016/0326187 A1 Nov. 10, 2016

(51) Int. Cl.
*C07F 1/12* (2006.01)
(52) U.S. Cl.
CPC .................................. *C07F 1/12* (2013.01)

(58) Field of Classification Search
CPC ........................................................ C07F 1/12
See application file for complete search history.

(56) References Cited

PUBLICATIONS

Boscutti et al. "t-Butylsarcosinedithiocarbamato gold(III)-based anticancer agents: Design, in vitro biological evaluation and interaction with model biomolecules" Inorganica Chimica Acta, 2012, vol. 393, pp. 304-317.*
Naeem et al. "Ring-Closing Metathesis and Nanoparticle Formation Based on Diallyldithiocarbamate Complexes of Gold(I): Synthetic, Structural, and Computational Studies" Inorganic Chemistry, 2014, vol. 53, pp. 2404-2416.*

\* cited by examiner

*Primary Examiner* — Joseph Kosack
(74) *Attorney, Agent, or Firm* — Oblon, McClelland, Maier & Neustadt, L.L.P.

(57) ABSTRACT

Monomeric gold(I) complexes as anticancer agents. The gold(I) complexes are coordinated to mixed ligands: one N-heterocyclic carbene ligand and one monodentate dithiocarbamate-based ligand. Pharmaceutical compositions incorporating the gold(I) complexes, methods of synthesis, methods of treating cancer and methods of inhibiting cancer cell proliferation and inducing cancer cell apoptosis are also provided.

11 Claims, 17 Drawing Sheets

N-HETEROCYCLIC CARBENE GOLD COMPLEXES WITH ANTICANCER PROPERTIES AND METHODS OF USE THEREOF

STATEMENT OF ACKNOWLEDGEMENT

This project was funded by the National Plan for Science, Technology and Innovation (MAARIFAH)—King Abdulaziz City for Science and Technology—the Kingdom of Saudi Arabia, award number (11-MED1670-04).

BACKGROUND OF THE INVENTION

Technical Field

The present invention relates to N-heterocyclic carbene gold(I) dithiocarbamate complexes with anticancer or antitumor properties, and pharmaceutical compositions and uses thereof.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Organometallic compounds of coinage metals (Cu, Ag and Au) have extensively been investigated owing to their diverse applications in bioinorganic and medicinal chemistry. Among coinage metals, gold complexes have attracted considerable attention in the treatment of many chronic diseases, such as rheumatoid arthritis, bronchial asthma and cancer due to their physicochemical, biological and pharmacological properties. Both gold(I) and gold(III) complexes bearing different functional ligands have numerous bio-medical applications [K. Nomiya, R. S. Yamamoto, Noghuchi, H. Yokoyama, N. C. Kasuga, K. Ohyama, C. Kato, J. Inorg. Biochem. 95 (2003) 208-220; T. McCormick, W.-L. Jia, S. Wang, Inorg. Chem. 45 (2006) 147-155; S. S. Al-Jaroudi, M. I. M. Wazeer, A. A. Isab, S. Altuwaijri, Polyhedron (2013) 434-442; R. B. Bostancioglu, K. Isik, H. Genc, K. Benkli, A. T. Koparal, Med. Chem. 27 (2012) 458-466—each incorporated herein by reference in their entirety].

Gold(I) complexes are potential chrysotherapeutic agents, which manifest outstanding antiproliferative activity against specific human cancer cell lines that are resistant or sensitive to classical chemotherapeutic platinum drugs [S. H. van Rijt, P. J. Sadler, Drug Discov. Today 14 (2009) 1089-1097—incorporated herein by reference in its entirety]. The novelty of Au(I) based drugs is the characteristic molecular structure that allows them to overcome resistance pathways, which were encountered in platinum-based chemotherapy. DNA is not a major pharmacological target of gold-based drugs, rather, the inhibition of other enzymes are involved.

Applications of gold carbene complexes are beginning to emerge in the medicinal and biochemical fields [H. G. Raubenheimer, S. Cronje, Chem. Soc. Rev. 37 (2008) 1998-2011—incorporated herein by reference in its entirety]. The antiarthritic gold(I) phosphine compound, auranofin (AF) shows interesting antitumor in vitro as well as in vivo activity. It also inhibits glutathione S-transferase expression in several chemoresistant tumors [R. Noghuchi, A. Hara, A. Sugie, K. Nomiya, Inorg. Chem. Commun. 9 (2006) 355-359—incorporated herein by reference in its entirety]. Ott pointed out that N-heterocyclic carbenes (NHCs) are an interesting class of ligands that mimic phosphines with donor properties [I. Ott, Coord. Chem. Rev. 253 (2009) 1670-1681—incorporated herein by reference in its entirety]. Baker et al. reported the mononuclear, cationic, linear Au(I) N-heterocyclic carbene species induce dose-dependent mitochondrial swelling in an isolated rat liver [M. V. Baker, P. J. Barnard, S. J. Berners-Price, S. K. Brayshaw, J. L. Hickey, B. W. Skelton, A. H. White, Dalton Trans. 30 (2006) 3708-3715—incorporated herein by reference in its entirety]. Barnad et al. also described a series of bis-NHC-gold(I) complexes that induce mitochondrial swelling, which was directly affected by lipophilicity [P. J. Barnard, S. J. Berners-Price, Coord. Chem. Rev. 251 (2007) 1889-1902—incorporated herein by reference in its entirety]. Siciliano et al. prepared bis(1,3-dimethylimidazol-2-ylidene) gold(I) nitrate and bis(4,5-dichloro-1,3-dimethyl-imidazol-2-ylidene)gold(I) nitrate salts via transmetallation of their silver precursors with chloro dimethylsulfide gold and determined the anticancer properties using NCI-H460 lung cancer cells [T. J. Siciliano, M. C. Deblock, K. M. Hindi, S. Durmus, M. J. Panzner, C. A. Tessier, W. J. Youngs, J. Organomet. Chem. 696 (2011) 1066-1071—incorporated herein by reference in its entirety].

Gold complexes with dithiocarbamate ligands have also emerged as anticancer agents and have shown much promising results [G. Boscutti, L. Feltrin, D. Lorenzon, S. Sitran, D. Aldinucci, L. Ronconi, D. Fregona, Inorg. Chim. Acta 393 (2012) 304-317—incorporated herein by reference in its entirety]. Ronconi et al. prepared and characterized some novel gold(III) dithiocarbamate compounds containing N,N-dimethyldithiocarbamate and ethyl sarcosine dithiocarbamate, demonstrating very encouraging chemical and biological profiles [L. Ronconi, L. Giovagnini, C. Marzano, F. Bettio, R. Graziani, G. Pilloni, D. Fregona, Inorg. Chem. 44 (2005) 1867-1881—incorporated herein by reference in its entirety]. Further, the treatment with dibromo(N,N-dimethyldithiocarbamato) gold(III) complex resulted in significant inhibition of in vivo MDA-MB-231 breast tumor growth [V. Milacic, D. Chen, L. Ronconi, K. R. Landis-Piwowar, D. Fregona, Q. P. Dou, Cancer Res. 66 (2006) 10478-10486—incorporated herein by reference in its entirety]. Zhang et al. reported gold(I)-dithiocarbamato species, namely [Au(ESDT)] could inhibit the chymotrypsin-like activity of purified 20S proteasome and 26S proteasome in human breast cancer MDA-MB-231 cells [X. Zhang, M. Frezza, V. Milacic, L. Ronconi, Y. Fan, C. Bi, D. Fregona, Q. P. Dou, J. Cell. Biochem. 109 (2010) 162-172—incorporated herein by reference in its entirety].

Worldwide, lung and colorectal cancers are common causes of cancer-related death in men and women while cervical cancer is a major cause of cancer death among women [K. Nomiya, R. Noghuchi, K. Ohsawa, K. Tsuda, M. Oda, J. Inorg. Biochem. 78 (2000) 363-370—incorporated herein by reference in its entirety]. Chemotherapy is still the primary method for treating cancers followed by radiotherapy. Nevertheless, there are some major challenges for treating cancers which include intrinsic resistance of cancer to chemotherapy, different phenotypes of cancer, and systemic toxicity issues. Therefore, new chemotherapeutic modalities are required. New gold carbene complexes are being developed by incorporating activity-enhancing and bio-acceptable co-ligands like dithiocarbamate with specific inherent properties for biomedical applications. Based on this strategy, a novel series of gold(I) complexes may be developed with new combination of C and S donor atoms of carbene and dithiocarbamate ligands respectively that show enhanced selectivity for such resistant cancers and with fewer side-effects in comparison to platinum-based drugs.

In view of the forgoing, the objective of the present disclosure is to provide N-heterocyclic carbene gold(I) dithiocarbamate complexes with efficacy against, and selectivity towards, cancers that are resistant to platinum-based chemotherapeutic agents, while also providing fewer side effects.

BRIEF SUMMARY OF THE INVENTION

According to a first aspect, the present disclosure relates to a N-heterocyclic carbene-gold(I) dithiocarbamate complex of formula I

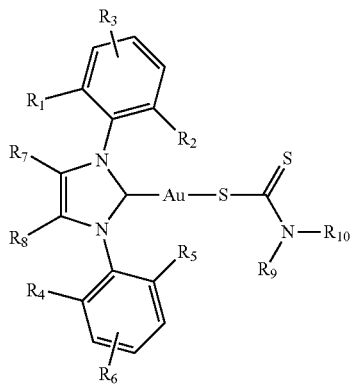

(I)

or a pharmaceutically acceptable salt, solvate, or prodrug thereof wherein:

$R_1$, $R_2$, $R_3$, $R_4$, $R_5$, $R_6$, $R_7$, $R_8$ are each independently a hydrogen, an optionally substituted alkyl, an optionally substituted cycloalkyl, an optionally substituted heterocyclyl, an optionally substituted arylalkyl, an optionally substituted heteroaryl, an optionally substituted alkoxyl, an optionally substituted thioalkoxyl, an optionally substituted aryl, a N-monosubstituted amino group, or a N,N-disubstituted amino group; and $R_9$ and $R_{10}$ are each independently a hydrogen, an optionally substituted $C_1$-$C_8$ alkyl, an optionally substituted cycloalkyl, an optionally substituted heterocyclyl, an optionally substituted arylalkyl, an optionally substituted heteroaryl, an optionally substituted alkoxyl, an optionally substituted aryl, a N-monosubstituted amino group, or a N,N-disubstituted amino group.

In one embodiment, $R_1$, $R_2$, $R_4$, and $R_5$ are each methyl, ethyl, isopropyl or t-butyl. $R_3$, $R_6$, $R_7$, and $R_8$ are hydrogen. $R_9$ and $R_{10}$ are each methyl, ethyl, isopropyl, benzyl, or phenyl.

In one embodiment, the N-heterocyclic carbene-gold(I) dithiocarbamate complex of formula I is

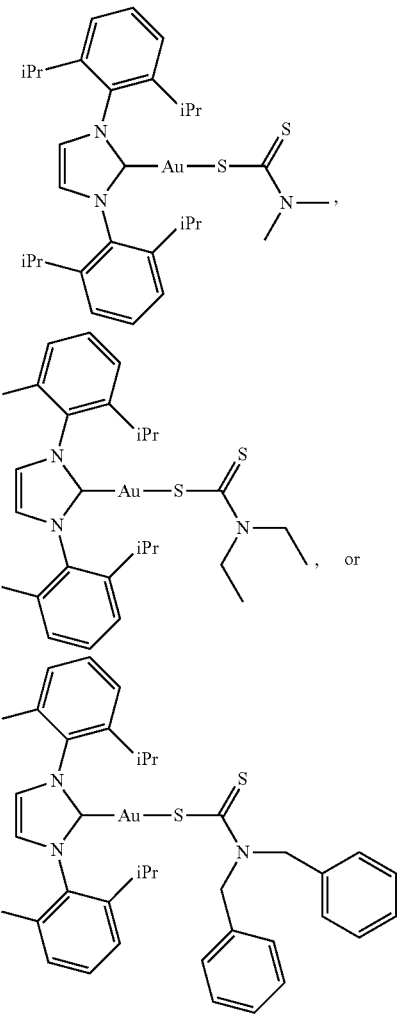

In one embodiment, the complex of formula I has in vitro cytotoxic activity against A549, HeLa, HCT15 and cancer cell lines with an $IC_{50}$ value that does not exceed 160 μM.

According to a second aspect, the present disclosure relates to a pharmaceutical composition, including the N-heterocyclic carbene-gold(I) dithiocarbamate complex of formula I or a pharmaceutically acceptable salt, solvate, or prodrug thereof, and a pharmaceutically acceptable carrier or excipient.

In one embodiment, the pharmaceutical composition further comprises one or more other active pharmaceutical agents.

In one embodiment, the pharmaceutical composition is in solid, semi-solid or liquid dosage forms.

In one embodiment, the pharmaceutical composition is formulated for at least one mode of administration selected from the group consisting of oral administration, systemic administration, parenteral administration, inhalation spray, infusion, rectal administration, topical administration, intravesical administration, intradermal administration, transdermal administration, subcutaneous administration, intramuscular administration, intralesional administration, intracranial administration, intrapulmonal administration, intracardial administration, intrasternal administration and sublingual administration.

According to a third aspect, the present disclosure relates to a method for the treatment of a proliferative disorder in a patient, involving administering to the patient a therapeutically effective amount of the N-heterocyclic carbene-gold(I) dithiocarbamate complex of formula I or a pharmaceutically acceptable salt, solvate, or prodrug thereof.

In one embodiment, the proliferative disorder is cancer.

In one embodiment, the cancer is lung, cervix, and/or colon cancer.

In one embodiment, the N-heterocyclic carbene-gold(I) dithiocarbamate complex exhibits an $IC_{50}$ value that does not exceed 160 µM against lung, cervix, or colon cancer.

In one embodiment, the administering is by oral administration, systemic administration, parenteral administration, inhalation spray, infusion, rectal administration, topical administration, intravesical administration, intradermal administration, transdermal administration, subcutaneous administration, intramuscular administration, intralesional administration, intracranial administration, intrapulmonal administration, intracardial administration, intrasternal administration, or sublingual administration.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
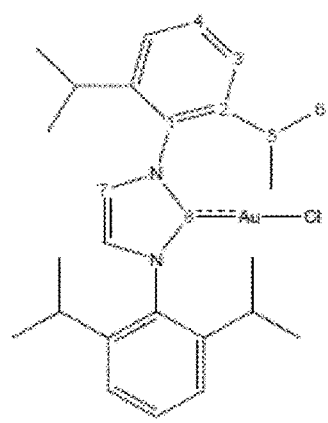
FIG. 1A is a skeletal structure of complex 0 [(Ipr)Au(Cl)].

Embodiments of the present disclosure will now be described more fully hereinafter with reference to the accompanying drawings, in which some, but not all embodiments of the disclosure are shown.

The present disclosure will be better understood with reference to the following definitions:

As used herein, "compound" and "complex" are intended to refer to a chemical entity, whether in the solid, liquid or gaseous phase, and whether in a crude mixture or purified and isolated.

The term "alkyl", as used herein, unless otherwise specified, refers to a saturated straight, branched, or cyclic, primary, secondary, or tertiary hydrocarbon of typically $C_1$ to $C_8$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term optionally includes substituted alkyl groups. Moieties with which the alkyl group can be substituted are selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

The term "aryl", as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis [Harper, N.J. (1962) Drug Latentiation in Jucker, ed. Progress in Drug Research, 4:221-294; Morozowich et al. (1977) Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977) Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, *Curr. Pharm. Design.* 5(4):265-287; Pauletti et al. (1997). Improvement in peptide bioavailability: Peptidomimetics and Prodrug Strategies, *Adv. Drug. Delivery Rev.* 27:235-256; Mizen et al. (1998) The Use of Esters as Prodrugs for Oral Delivery of β-Lactam antibiotics, *Pharm. Biotech.* 11:345-365; Gaignault et al. (1996) Designing Prodrugs and Bioprecursors I. Carrier Prodrugs, *Pract. Med. Chem.* 671-696; M. Asgharnejad (2000) Improving Oral Drug Transport Via Prodrugs, in G. L. Amidon, P. I. Lee and E. M. Topp, Eds., Transport Processes in Pharmaceutical. Systems, Marcell Dekker, p. 185-218; Balant et al. (1990) Prodrugs for the improvement of drug absorption via different routes of administration, *Eur. J. Drug Metab. Pharmacokinet.,* 15(2): 143-53; Balimane and Sinko (1999). Involvement of multiple transporters in the oral absorption of nucleoside analogs, *Adv. Drug Delivery Rev.,* 39(1-3):183-209; Browne (1997) Fosphenyloin (Cerebyx), *Clin. Neuropharmacol.* 20(1): 1-12; Bundgaard (1979) Bioreversible derivatization of drugs—principle and applicability to improve the therapeutic effects of drugs, *Arch. Pharm. Chemi.* 86(1): 1-39; H. Bundgaard, ed. (1985) Design of Prodrugs, New York: Elsevier; Fleisher et al. (1996). Improved oral drug delivery: solubility limitations overcome by the use of prodrugs, *Adv. Drug Delivery Rev.* 19(2): 115-130; Fleisher et al. (1985). Design of prodrugs for improved gastrointestinal absorption by intestinal enzyme targeting, *Methods Enzymol.* 112: 360-81; Farquhar D, et al. (1983). Biologically Reversible Phosphate-Protective Groups, *J. Pharm. Sci.,* 72(3): 324-325; Han, H. K. et al. (2000). Targeted prodrug design to optimize drug delivery, *AAPS PharmSci.,* 2(1): E6; Sadzuka Y. (2000). Effective prodrug liposome and conversion to active metabolite, *Curr. Drug Metab.,* 1(1):31-48; D. M. Lambert (2000) Rationale and applications of lipids as prodrug carriers, *Eur. J. Pharm. Sci.,* 11 Suppl 2:S15-27; Wang, W. et al. (1999) Prodrug approaches to the improved delivery of peptide drugs. *Curr. Pharm. Des.,* 5(4):265-87—each incorporated herein by reference in its entirety]. "Pharmaceutically acceptable prodrugs" refer to a compound that is metabolized, for example hydrolyzed or oxidized, in the host to form the pharmaceutical composition of the present disclosure. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines, and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred.

The term "solvate" means a physical association of a compound of this disclosure with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution-phase and isolable solvates. Exemplary solvates include, but are not limited to, hydrates, ethanolates, methanolates, and isopropanolates. Methods of solvation are generally known in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Therefore, the pharmaceutical composition refers to the combination of an active agent with a carrier, inert or active, making the composition especially suitable for diagnostic or therapeutic use in vivo or ex vivo.

The phrase "pharmaceutically acceptable carrier or excipient" as used herein means a pharmaceutically acceptable material, composition or vehicle, such as a liquid or solid filler, diluent, binder, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

As used herein, a "binder" holds the ingredients in a tablet together. Binders ensure that tablets and granules can be formed with required mechanical strength, and give volume to low active dose tablets. Binders may be: (1) saccharides and their derivatives, such as sucrose, lactose, starches, cellulose or modified cellulose such as microcrystalline cellulose, carboxymethyl cellulose, and cellulose ethers such as hydroxypropyl cellulose (HPC), and sugar alcohols such as xylitol, sorbitol or maltitol (2) proteins such as gelatin and (3) synthetic polymers including polyvinylpyrrolidone (PVP), polyethylene glycol (PEG). Binders are classified according to their application. Solution binders are dissolved in a solvent (for example water or alcohol can be used in wet granulation processes). Examples include gelatin, cellulose, cellulose derivatives, polyvinylpyrrolidone, starch, sucrose and polyethylene glycol. Dry binders are added to the powder blend, either after a wet granulation step, or as part of a direct powder compression (DC) formula. Examples include cellulose, methyl cellulose, polyvinylpyrrolidone and polyethylene glycol.

The term "therapeutically effective amount" as used herein refers to that amount of the compound being administered which will relieve to some extent one or more of the symptoms of the disorder being treated. In reference to cancer or pathologies related to increased cell division, a therapeutically effective amount refers to that amount which has the effect of at least one of the following: (1) reducing the size of a tumor, (2) inhibiting (that is, slowing to some extent, preferably stopping) aberrant cell division, growth or proliferation, for example cancer cell division, (3) preventing or reducing the metastasis of cancer cells, (4) relieving to some extent (or, preferably, eliminating) one or more symptoms associated with a pathology related to or caused in part by unregulated or aberrant cellular division, including for example, cancer and (5) inducing apoptosis of cancer cells or tumor cells.

As used herein, the terms "therapies" and "therapy" can refer to any method(s), composition(s), and/or agent(s) that can be used in the prevention, treatment and/or management of a cancer or one or more symptoms thereof.

As used herein, the terms "treat," "treatment," and "treating" in the context of the administration of a therapy to a subject in need thereof refer to the reduction or inhibition of the progression and/or duration of cancer, the reduction or amelioration of the severity of cancer, and/or the amelioration of one or more symptoms thereof resulting from the administration of one or more therapies. In some embodiments, the subject is a mammalian subject. In one embodiment, the subject is a human. "Treating" or "treatment" of a disease includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer or hyperplasia, these terms simply mean that the life expectancy of an individual affected with a cancer will be increased or that one or more of the symptoms of the disease will be reduced. In specific embodiments, such terms refer to one, two or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, and (12) an increase in the number of patients in remission. In certain embodiments, such terms refer to a stabilization or reduction in the cancer stem cell population. In some embodiments, such terms refer to a stabilization or reduction in the growth of cancer cells. In some embodiments, such terms refer to stabilization or reduction in the cancer stem cell population and a reduction in the cancer cell population. In some embodiments, such terms refer to a stabilization or reduction in the growth and/or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in survival rate of a patient population. In further embodiments, such terms refer to an increase in the response rate, the durability of response, or number of patients who respond or are in remission. In some embodiments, such terms refer to a decrease in hospitalization rate of a patient population and/or a decrease in hospitalization length for a patient population.

The present disclosure provides mono-gold(I) complexes having medicinal or pharmaceutical properties, preferably antitumor or anticancer properties. In these monomeric gold(I) complexes, each gold(I) atom is coordinated, preferably coordinated by two or more mixed ligands that are based on dithiocarbamate and N-heterocyclic carbene functional groups as shown below:

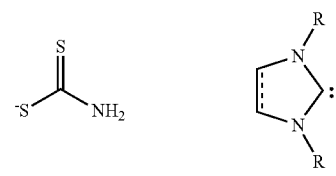

dithiocarbamate     N-heterocyclic carbene

The dithiocarbamate-based ligand coordinates a gold(I) atom in a monodentate manner. The nitrogen atom of a dithiocarbamate-based ligand can be substituted with one or more alkyl or aryl groups, for example, substituted or unsubstituted $C_1$-$C_8$ alkyl groups or substituted or unsubstituted $C_6$-$C_8$ aryl groups.

A carbene is a molecule containing a neutral carbon atom with a valence of two and two unshared valence electrons. The most common types of persistent carbenes are the subclass referred to as N-heterocyclic carbenes, where the carbene carbon center is part of a heterocyclic ring system and adjacent to at least one nitrogen atom (e.g. imidazoline-based N-heterocyclic carbenes).

According to a first aspect, the present disclosure relates to a N-heterocyclic carbene-gold(I) dithiocarbamate complex of formula I

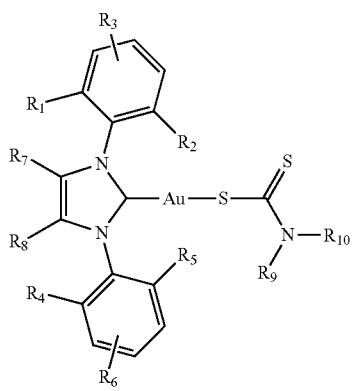

(I)

or a pharmaceutically acceptable salt, solvate, or prodrug thereof
wherein:

$R_1$, $R_2$, $R_3$, $R_4$, $R_5$, $R_6$, $R_7$, $R_8$ are each independently a hydrogen, an optionally substituted alkyl, an optionally substituted cycloalkyl, an optionally substituted heterocyclyl, an optionally substituted arylalkyl, an optionally substituted heteroaryl, an optionally substituted alkoxyl, an optionally substituted thioalkoxyl, an optionally substituted aryl, a N-monosubstituted amino group, or a N,N-disubstituted amino group; and $R_9$ and $R_{10}$ are each independently a hydrogen, an optionally substituted $C_1$-$C_8$ alkyl, an optionally substituted cycloalkyl, an optionally substituted heterocyclyl, an optionally substituted arylalkyl, an optionally substituted heteroaryl, an optionally substituted alkoxyl, an optionally substituted aryl, a N-monosubstituted amino group, or a N,N-disubstituted amino group.

In one embodiment, the N-heterocyclic carbene ligand is an imidazoline-based carbene ligand. The imidazoline-based carbene ligand may be saturated, or alternatively and preferably, the imidazoline is unsaturated. Alternatively, the present disclosure may be adapted to incorporate other types of carbene ligands, including, but not limited to imidazole-based, triazole-based, chalcogen-based, and thiazole-based carbene ligands.

In one embodiment, the present disclosure provides a process for making a complex of the present disclosure or a salt, solvate, or prodrug thereof. The compounds of formula I may generally be prepared by a ligand metathesis reaction from N-heterocyclic carbene-gold(I) chloride complexes, which is known to those of ordinary skill. Methods of solvation are also generally known in the art.

In one embodiment, $R_1$, $R_2$, $R_4$, and $R_5$ are each methyl, ethyl, isopropyl or t-butyl. $R_3$, $R_6$, $R_7$, and $R_8$ are hydrogen. $R_9$ and $R_{10}$ are each methyl, ethyl, isopropyl, benzyl, or phenyl.

In one embodiment, the N-heterocyclic carbene-gold(I) dithiocarbamate complex of formula I is

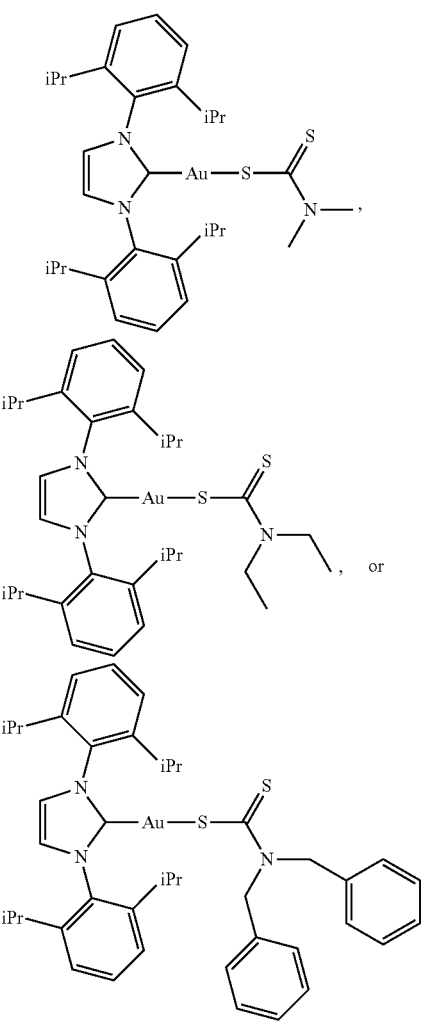

In terms of the present disclosure, the term "Ipr" refers to the unsaturated imidazol-2-ylidene ligands where $R_1$, $R_2$, $R_4$, $R_5$ are isopropyl substituents. A monomeric N-heterocyclic carbene gold(I) dithiocarbamate complex contains one Ipr-Au—P motif, where the bond distance between Au—S and Au-Ipr are equal or nearly equal to each other at 1.8-2.7 Å, preferably 1.9-2.5 Å, more preferably 1.95-2.35 Å.

In one embodiment, the complex of formula I has in vitro cytotoxic activity against A549, HeLa, HCT15 and cancer cell lines with an $IC_{50}$ value that does not exceed 160 μM, preferably that does not exceed 150 μM, more preferably that does not exceed 140 μM.

The present disclosure is intended to include all isotopes of atoms occurring in the present complexes. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed.

According to a second aspect, the present disclosure relates to a pharmaceutical composition, including the N-heterocyclic carbene-gold(I) dithiocarbamate complex of formula I or a pharmaceutically acceptable salt, solvate, or prodrug thereof, and a pharmaceutically acceptable carrier or excipient.

In one embodiment, the pharmaceutical composition further comprises one or more other active pharmaceutical agents. Exemplary pharmaceutical agents include, but is not limited to chemotherapeutic agents aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cis-platin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguanine), tipifarnib. Examples for antineoplastic agents which are protein kinase inhibitors include imatinib, erlotinib, sorafenib, sunitinib, dasatinib, nilotinib, lapatinib, gefitinib, temsirolimus, everolimus, rapamycine, bosutinib, pzopanib, axitinib, neratinib, vatalanib, pazopanib, midostaurin and enzastaurin. Examples for antineoplastic agents which are antibodies comprise trastuzumab, cetuximab, panitumumab, rituximab, bevacizumab, mapatumumab, conatumumab, lexatumumab and the like.

In one embodiment, the pharmaceutical composition is in solid, semi-solid or liquid dosage forms.

In one embodiment, the pharmaceutical composition is formulated for at least one mode of administration selected from the group consisting of oral administration, systemic administration, parenteral administration, inhalation spray, infusion, rectal administration, topical administration, intravesical administration, intradermal administration, transdermal administration, subcutaneous administration, intramuscular administration, intralesional administration, intracranial administration, intrapulmonal administration, intracardial administration, intrasternal administration and sublingual administration.

In one embodiment, the present disclosure provides a pharmaceutical composition, comprising a pharmaceutically acceptable carrier and a therapeutically effective amount of at least one of the complexes of the present disclosure or a pharmaceutically acceptable salt, solvate, or prodrug thereof.

In one embodiment, the pharmaceutical composition comprises 1-99.9%, preferably 10-99.9%, more preferably 20-99.9%, more preferably 30-99.9%, more preferably 40-99.9%, more preferably 50-99.9%, more preferably 60-99.9%, more preferably 70-99.9%, more preferably 80-99.9%, even more preferably 90-99.9% of the complex of formula I, and 0.1% or more of the pharmaceutically acceptable carrier or excipient, based on the total weight of the composition.

Methods of preparing these formulations or compositions include the step of bringing into association a complex of the present disclosure with the carrier and, optionally, one or more accessory ingredients. In general, the formulations are prepared by uniformly and intimately bringing into association a complex of the present disclosure with liquid carriers, or finely divided solid carriers, or both, and then, if necessary, shaping the product.

Formulations of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a complex of the present disclosure as an active ingredient. A complex of the present disclosure may also be administered as a bolus, electuary or paste.

Pharmaceutical compositions of this disclosure suitable for parenteral administration comprise one or more complexes of the disclosure in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful. Suppositories for rectal administration of the compound or an analog or derivative thereof can be prepared by mixing the steroid or an analog or derivative thereof with a suitable nonirritating excipient such as cocoa butter, synthetic mono- di- or triglycerides, fatty acids and polyethylene glycols that are solid at ordinary temperatures but liquid at the rectal temperature and will therefore melt in the rectum and release the drug.

If administered per os, a gold complex of formula I can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

When the complexes of the present disclosure are administered as pharmaceuticals, to humans and animals, they can be given per se or as a pharmaceutical composition containing, for example, 1-99.9%, preferably 10-99.9%, more preferably 20-99.9%, more preferably 30-99.9%, more preferably 40-99.9%, more preferably 50-99.9%, more preferably 60-99.9%, more preferably 70-99.9%, more preferably 80-99.9%, even more preferably 90-99.9% of active ingredient in combination with a pharmaceutically acceptable carrier.

Regardless of the route of administration selected, the complexes of the present disclosure, which may be used in a suitable hydrated form, and/or the pharmaceutical compositions of the present disclosure, are formulated into pharmaceutically acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient. A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

According to a third aspect, the present disclosure relates to a method for the treatment of a proliferative disorder in a patient, involving administering to the patient a therapeutically effective amount of the N-heterocyclic carbene-gold(I) dithiocarbamate complex of formula I or a pharmaceutically acceptable salt, solvate, or prodrug thereof.

In one embodiment, the proliferative disorder is cancer.

The neoplastic activity of the tumor or cancer cells may be localized or initiated in one or more of the following: blood, brain, bladder, lung, cervix, ovary, colon, rectum, pancreas, skin, prostate gland, stomach, breast, liver, spleen, kidney, head, neck, testicle, bone (including bone marrow), thyroid gland, central nervous system. The N-heterocyclic carbene gold(I) dithiocarbamate complex of the present disclosure or the pharmaceutical composition thereof is especially effective in the treatment or prevention of colorectal cancer (including colon cancer, rectum cancer and bowel cancer); lung cancer (including non-small cell lung carcinoma or NSCLC and small cell lung carcinoma); cervical cancer (including the histologic subtypes of squamous cell carcinoma, adenocarcinoma, adenosquamous carcinoma, small cell carcinoma, neuroendocrine tumor, glass cell carcinoma, villoglandular adenocarcinoma, melanoma and lymphoma).

Cancers such as, but not limited to sarcomas, carcinomas, melanomas, myelomas, gliomas and lymphomas can be treated or prevented with the gold(I) complexes provided herein. In some embodiments, methods incorporating the use of at least one of the gold(I) complexes of the present disclosure are effective in the treatment or prevention of cancer of the blood, brain, bladder, lung, cervix, ovary, colon, rectum, pancreas, skin, prostate gland, stomach, breast, liver, spleen, kidney, head, neck, testicle, bone (including bone marrow), thyroid gland or central nervous system. In some embodiments, these methods are especially effective in the treatment or prevention of cervical, colon and lung cancers.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, after treatment with one or more gold(I) complexes or a pharmaceutical composition thereof, the size of a tumor, whether by volume, weight or diameter, is reduced by at least 5%, 10%, 15%, 20%, 25%, 30%, 40%, 50%, 60%, 70%, 75%, 80%, 85%, 90%, 95%, 99% or 100%, relative to the tumor size before treatment. In other embodiments, after treatment with the one or more gold(I) complexes of a pharmaceutical composition thereof, the size of a tumor does not reduce but is maintained the same as the tumor size before treatment. Methods of assessing tumor size include but are not limited to CT Scan, MRI, DCE-MRI and PET Scan.

In some embodiments, the method for treating cancer and other proliferative disorders involves the administration of a unit dosage or a therapeutically effective amount of one or more of gold(I) complexes or a pharmaceutical composition thereof to a mammalian subject (preferably a human subject) in need thereof. As used herein, "a subject in need thereof" refers to a mammalian subject, preferably a human subject, who has been diagnosed with, is suspected of having, is susceptible to, is genetically predisposed to or is at risk of having at least one form of cancer. Routes or modes of administration are as set forth herein. The dosage and treatment duration are dependent on factors such as bioavailability of a drug, administration mode, toxicity of a drug, gender, age, lifestyle, body weight, the use of other drugs and dietary supplements, cancer stage, tolerance and resistance of the body to the administered drug, etc., then determined and adjusted accordingly. The one or more of gold(I) complexes or a pharmaceutical composition thereof may be administered in a single dose or multiple individual divided doses. In some embodiments, the interval of time between the administration of gold(I) complexes or a pharmaceutical composition thereof and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, the gold(I) compounds provided herein and one or more additional therapies are administered less than 1 day, 1 week, 2 weeks, 3 weeks, 4 weeks, one month, 2 months, 3 months, 6 months, 1 year, 2 years, or 5 years apart.

Human cancer cells are contacted with 1-100 µM of a gold(I) complex of formula I in accordance with the present disclosure or a composition comprising the gold(I) complex at the defined concentration range, preferably 2-75 µM, more preferably 5-50 µM.

In one embodiment, the N-heterocyclic carbene-gold(I) dithiocarbamate complex exhibits an $IC_{50}$ value that does not exceed 160 μM, preferably that does not exceed 150 μM, more preferably that does not exceed 140 μM against lung, cervix, or colon cancer. Upon contacting cancer cells to the complexes of the present disclosure, the cancer cells may undergo apoptosis. In this scenario, the viability of these cells can be determined by standard cell viability assays such as but not limited to ATP test, Calcein AM assay, clonogenic assay, ethidium homodimer assay, Evans blue assay, Fluorescein diacetate hydrolysis/propidium iodide staining assay, flow cytometry assay, formazan-based assays (MTT.XTT), green fluorescent protein assay, lactate dehydrogenase assay, methyl vilet assay, propidium iodide assay, Resazurin assay, Trypan Blue assay and TUNEL assay.

When contacted with the gold(I) complex at the defined concentration, the viability of the human cancer cells is reduced to at least 95%, preferably at least 85%, more preferably at least 75%, even more preferably at least 50%, at least 45%, at least 40%, at least 35%, at least 30%, at least 25%, at least 20%, most preferably at least 15%, at least 12.5%, at least 10%, at least 7.5%, at least 5%, at least 2.5%, at least 2%, at least 1% and at least 0.5%.

Any method of administration may be used to deliver the complex of formula I or pharmaceutical composition thereof to the patient. The disclosure also provides pharmaceutically acceptable compositions which comprise a therapeutically effective amount of one or more of the complexes of formula I, formulated together with one or more pharmaceutically acceptable carriers (additives) and/or diluents, and optionally, one or more additional therapeutic agents. In one embodiment, the administering is by oral administration, systemic administration, parenteral administration, inhalation spray, infusion, rectal administration, topical administration, intravesical administration, intradermal administration, transdermal administration, subcutaneous administration, intramuscular administration, intralesional administration, intracranial administration, intrapulmonal administration, intracardial administration, intrasternal administration, or sublingual administration. In one embodiment, the complex of the present disclosure, in one or more of its embodiments, is administered by injection or oral administration.

Topical administration can also involve the use of transdermal administration such as transdermal patches or iontophoresis devices. The term parenteral as used herein includes intravesical, intradermal, transdermal, subcutaneous, intramuscular, intralesional, intracranial, intrapulmonal, intracardial, intrasternal and sublingual injections, or infusion techniques. Formulation of drugs is discussed in, for example, Hoover, John E., Remington's Pharmaceutical Sciences, Mack Publishing Co., Easton, Pa.; 1975. Another example of includes Liberman, H. A. and Lachman, L., Eds., Pharmaceutical Dosage Forms, Marcel Decker, New York, N.Y., 1980, which is incorporated herein by reference in its entirety.

In one embodiment, the present disclosure provides a combined preparation of a complex of the present disclosure and additional therapeutic agent(s) for simultaneous, separate or sequential use in therapy. In particular, it is contemplated that complexes of the disclosure may be useful in combination with current Standards of Care as well as any that evolve over the foreseeable future. Specific dosages and dosing regimens would be based on physicians' evolving knowledge and the general skill in the art. The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In certain embodiments, a gold(I) complex of the present disclosure or a pharmaceutical composition thereof may be used in combination with one or more other antineoplastic or chemotherapeutic agents. A non-limiting list of examples of chemotherapeutic agents are aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cis-platin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguanine), tipifarnib. Examples for antineoplastic agents which are protein kinase inhibitors include imatinib, erlotinib, sorafenib, sunitinib, dasatinib, nilotinib, lapatinib, gefitinib, temsirolimus, everolimus, rapamycine, bosutinib, pzopanib, axitinib, neratinib, vatalanib, pazopanib, midostaurin and enzastaurin. Examples for antineoplastic agents which are antibodies comprise trastuzumab, cetuximab, panitumumab, rituximab, bevacizumab, mapatumumab, conatumumab, lexatumumab and the like.

Example 1

Results and Discussions

Spectroscopic Characterization

Dithiocarbamate compounds exhibited characteristic band in the 1480-1550 $cm^{-1}$ region attributed to the ν(C—N) and ν(C—S) stretching vibration [A. J. Odola, J. A. O. Woods, J. Chem. Pharm. Res. 3 (2011) 865-871—incorporated hereby by reference in its entirety]. The most prominent bands for complexes 1-3 (FIG. 1B-FIG. 1D) were observed at 1470 cm$^{-1}$, 1471 cm$^{-1}$ and 1473 cm$^{-1}$, respectively ascribed to the thioureide band, $\nu$(C—N). Since these frequency modes fell in between those associated with single C—N and double C=N bonds, hence the partial double bond character of 'thioureide' bond was confirmed for all complexes [F. Jian, Z. Wang, Z. Bai, X. You, H. Fun, K. Chinnakali, L. A. Razak, Polyhedron 18 (1999) 3401-3406—incorporated herein by reference in its entirety]. The presence of the thioureide band between 1545 and 1430 cm$^{-1}$, indicated a considerable double bond character in the C/N bond vibration of the S$_2$C—NR$_2$ group [A. Jayaraju, M. M. Ahamad, R. M. Rao, J. Sreeramulu, Der Pharma Chemica 4 (2012) 1191-1194—incorporated herein by reference in its entirety]. The stretching vibration from this partial double bond is due to the partial delocalization of electron density within the dithiocarbamate [H. Nabipour, S. Ghammamy, S. Ashuri, Z. S. Aghbolagh, J. Org. Chem. 2 (2010) 75-80—incorporated herein by reference in its entirety]. The C=S thio-carbonyl stretch in complexes 1-3 splits into two peaks (doublet) at 1058 cm$^{-1}$, 979 cm$^{-1}$, 1062 cm$^{-1}$, 991 cm$^{-1}$ and 1077 cm$^{-1}$, 975 cm$^{-1}$ with medium intensity, respectively. The presence of splitting to the $\nu$(C—S) bands in the range 975-991 cm$^{-1}$ indicates the monodentate nature of dialkyl dithiocarbamate ligands in the synthesized complexes [J. Chatt, L. A. Duncanson, L. M. Venanzi, Nature 177 (1956) 1042-1043; I. Raya, I. Baba, B. M. Yamin, Malaysia J. Anal. Sci. 10 (2006) 93-98; W. Haas, T. Schwarz, Microchem. Ichonal. Acta 58 (1963) 253-259; and D. C. Onwudiwe, P. A. Ajibade, Polyhedron 29 (2010) 1431-1436—each incorporated herein by reference in their entirety]. In addition to the polar thioureide ion bands S$_2$C=N$^+$R$_2$, the usual bands for sp$^3$ and sp$^2$ hybridized carbon-hydrogen stretches were observed ca. in the range 3000-2840 cm$^{-1}$ similar to the reported sodium salt of diethyldithiocarbamate [C. J. Pouchert, Aldrich Library of FT-IR Spectra, second ed., vol. 1, Aldrich Chemical Company, Milwaukee, 1997—incorporated herein by reference in its entirety]. Furthermore, the stretching bands attributed to the aromatic (phenyl) and saturated aliphatic C—H methyl group of coordinated dialkyl dithiocarbamate is in Table 1 [D. L. Pavia, G. M. Lampman, S. G. Kriz, Introduction to Spectrochemistry, third ed., Thomson Learning, USA., 2001, pp. 30-33; R. M. Silverstein, F. X. Webster, Spectrometric Identification of Organic Compounds, sixth ed., Wiley, New York, 1998; T. W. G. Solomons, C. Fryhle, Organic Chemistry, 7th edition upgrade, Wiley, New York, 2001; K. N. Kouroulis, S. K. Hadjikakou, N. Kourkoumelis, M. Kubicki, L. Male, M. Hursthouse, S. Skoulika, A. K. Metsios, V. Y. Tyurin, A. V. Dolganov, E. R. Milaevag, N. Hadjiliadis, J. Chem. Soc. Dalton Trans. (2009) 10446-10456; E. A. Allen, W. Wilkinson, Spectrochim. Acta 2 (1972) 2257-2262; I. S. Butler, A. Neppel, K. R. Plowman, C. F. Shaw, J. Raman Spectrosc. 15 (1984) 310-318; and A. G. Jones, D. B. Powell, Spectrochim. Acta 30 (1984) 563-570—each incorporated herein by reference in their entirety].

TABLE 1

Mid-IR frequencies (cm$^{-1}$) of complexes (1-3).

| Compound | Stretch C—H(CH$_3$) | Bend C—H(CH$_3$) | Stretch C—H(CH$_2$) | Bend C—H(CH$_2$) | Stretch C=S | Stretch S=C—N |
|---|---|---|---|---|---|---|
| Dimethyl dithiocarbamate | 2924 | 1360 | — | — | 962 | 1488 |
| (1) | 2961 (asym), 2866 (sym) | 1361 | — | — | 1058, 979 | 1470 |
| Diethyl dithiocarbamate | 2925 | 1358 | 2979 | 1379 | 986 | 1466 |
| (2) | 2962 (asym), 2867 (sym) | 1377 | 2926 | 1407 | 1062, 991 | 1473 |
| Dibenzyl dithiocarbamate | 2960 (asym), 2868 (sym) | 1347 | — | 1445 | 1075, 987 | 1491 |
| (3) | 2961 (asym), 2865 (sym) | 1395 | 2923 | 1451 | 1077, 975 | 1471 |

The $^1$H NMR chemical shifts of complexes 1-3 along with their corresponding metal precursor [(Ipr)Au(Cl), complex 0, FIG. 1A] and free dialkyl dithiocarbamate ligands are listed in Table 2. In all the complexes, a slight shift for proton(s) of the coordinated dimethyl dithiocarbamate, diethyl dithiocarbamate and dibenzyldithiocarbamate have been observed as compared to free dialkyl dithiocarbamate ligands. The $^{13}$C NMR chemical shifts of complexes 1-3 along with their corresponding metal precursor [(Ipr)Au(Cl), complex 0] and free dialkyl dithiocarbamate ligands are presented in Table 3. There are upfield chemical shifts of CH$_3$, CH$_2$ and C=S carbons of coordinated dialkyl dithiocarbamate with respect to free dialkyl dithiocarbamate ligands. The $^{13}$C chemical shifts of C=S carbon of dimethylthiocarbamate, dimethylthiocarbamate and dibenzyl thiocarbamate were observed in the range 206-213 ppm.

TABLE 2

Solution $^1$H NMR $\delta$ chemical shifts (ppm) and $^n$J coupling constants (Hz) of the free gold(I) metal precursor, free ligands and complexes (1-3).

| Compound | 3-H ppm | $^3J_{CH=CH}$ Hz | 4-H ppm | $^3J_{CH—CH}$ Hz | 5-H ppm | $^3J_{CH3—CH—CH3}$ Hz | 6-H' ppm |
|---|---|---|---|---|---|---|---|
| [Au(Ipr)(Cl)] | 7.39 | | 7.55 | | 2.46 | | |
| NaS$_2$CN(CH$_3$)$_2$•H$_2$O | — | | — | | — | | |
| (1) | 7.34 | 7.63 | 7.5 | 7.63 | 2.52 | 7.02 | 1.16 |
| NaS$_2$CN(C$_2$H$_5$)$_2$•3H$_2$O | — | | — | | — | | |
| (2) | 7.38 | 7.93 | 7.5 | 7.78 | 2.52 | 7.01 | 1.17 |
| NaS$_2$CN(CH$_7$H$_7$)$_2$•xH$_2$O | — | | — | | — | | |
| (3) | 7.33 | 7.93 | 7.5 | 7.63 | 2.53 | 7.02 | 1.15 |

TABLE 2-continued

Solution $^1$H NMR δ chemical shifts (ppm) and $^n$J coupling constants (Hz) of the free gold(I) metal precursor, free ligands and complexes (1-3).

| Compound | $^3J_{CH3-CH}$ Hz | 6-H ppm | $^3J_{CH3-CH}$ Hz | 7-H ppm | 10-H ppm | 11-H ppm | $^3J_{CH-CH}$ Hz |
|---|---|---|---|---|---|---|---|
| [Au(lpr)(Cl)] | | 1.21 | | 7.98 | — | — | |
| NaS$_2$CN(CH$_3$)$_2$·H$_2$O | | — | | — | 3.55 | — | |
| (1) | 7.02 | 1.25 | 6.71 | 7.91 | 3.12 | — | — |
| NaS$_2$CN(C$_2$H$_5$)$_2$·3H$_2$O | | — | | — | 4.03 | 1.23 | |
| (2) | 7.02 | 1.26 | 6.71 | 7.88 | 3.53 | 1 | 6.87 |
| NaS$_2$CN(CH$_7$H$_7$)$_2$·xH$_2$O | | — | | — | 4.98 | 7.01 | |
| (3) | 6.71 | 1.26 | 6.71 | 7.91 | 4.85 | 7.11 | 7.63 |

TABLE 3

Solution $^{13}$C NMR chemical shifts (ppm) of the free gold(I) metal precursor and Au(I) complexes (1), (2), and (3).

| Complex | C=S | Au=C | C-1 | C-2 | C-3 | C-4 | C-5 | C-6 | C-7 | C-10 | C-11 |
|---|---|---|---|---|---|---|---|---|---|---|---|
| [Au(lpr)(Cl)] | — | 172.86 | 134.06 | 145.32 | 124.55 | 124.09 | 28.37 | 23.5 | 130.52 | | |
| NaS$_2$CN(CH$_3$)$_2$·H$_2$O | 212.82 | — | — | — | — | — | — | — | — | 45.12 | — |
| (1) | 205.66 | 181.9 | 134.5 | 145.34 | 124.33 | 123.85 | 28.34 | 23.84 | 130.13 | 44.31 | — |
| NaS$_2$CN(C$_2$H$_5$)$_2$·3H$_2$O | 206.7 | — | — | — | — | — | — | — | — | 49.61 | 12.31 |
| (2) | 204.31 | 182.13 | 134.53 | 145.34 | 124.36 | 123.86 | 28.35 | 23.96 | 130.16 | 48 | 12.15 |
| NaS$_2$CN(C$_7$H$_7$)$_2$·H$_2$O | 213.53 | — | — | — | — | — | — | — | — | 56.9 | 127-137 |
| (3) | 208.28 | 181.61 | 134.52 | 145.35 | 124.45 | 123.9 | 28.39 | 23.89 | 130.17 | 55.37 | 127-136 |

Example 2

Crystal Structure Analysis

Crystal Structure of Complex [Au(Ipr)(S$_2$CN(CH$_3$)$_2$)] (1)

Figure 1B:
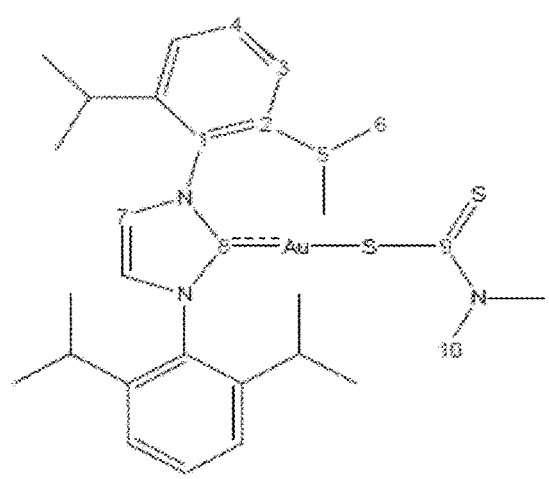
FIG. 1B is a skeletal structure of complex 1 [(Ipr)Au(S$_2$CN (CH$_3$)$_2$)].
Figure 1C:
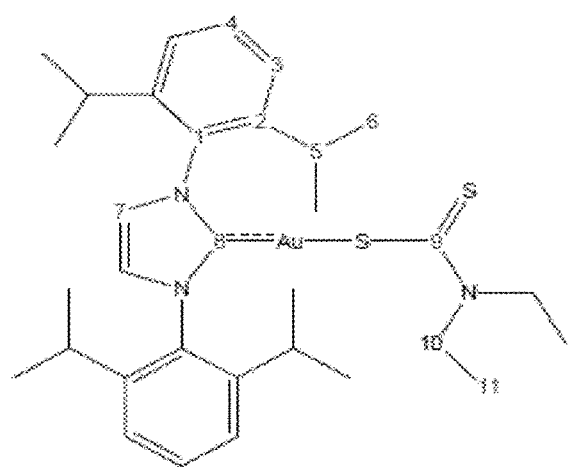
FIG. 1C is a skeletal structure of complex 2 [(Ipr)Au(S$_2$CN(C$_2$H$_5$)$_2$)].
Figure 2:
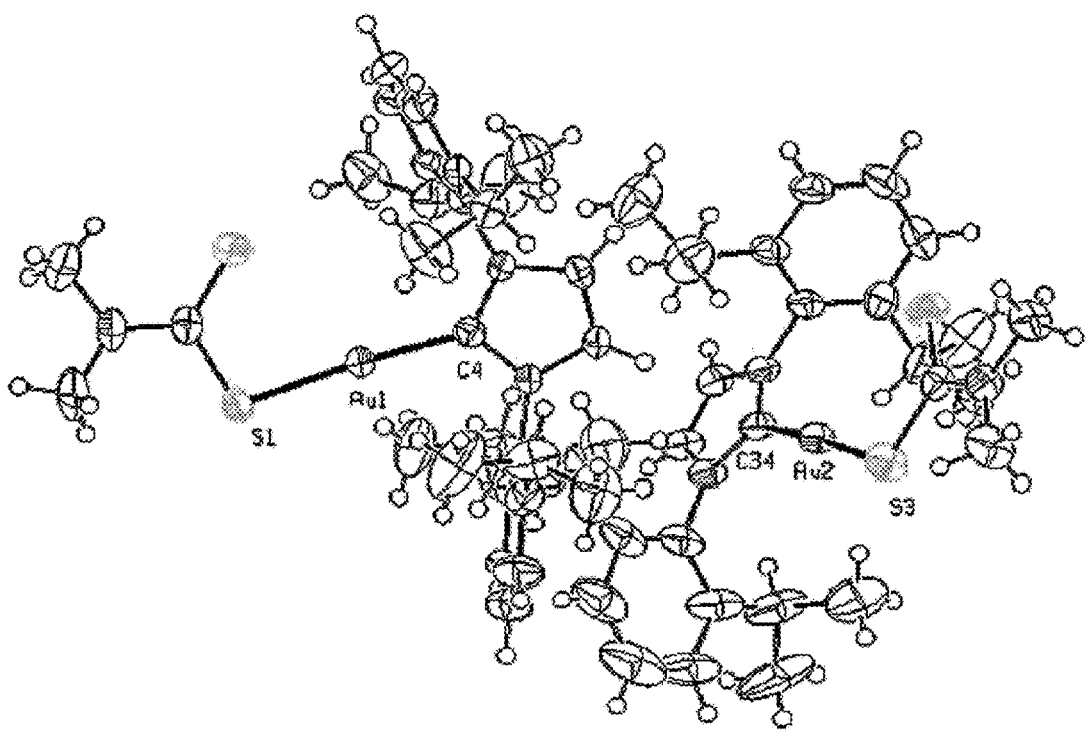
FIG. 2 is a view of the molecular structure of mononuclear complex 1 [(Ipr)Au(S$_2$CN(CH$_3$)$_2$)], with atom labeling scheme and displacement ellipsoids drawn at 50% probability level.

The molecular structure of complex [Au(Ipr)(S$_2$CN(CH$_3$)$_2$)] (1) is shown in FIG. 1B. In the asymmetric unit, there are two molecules with same geometry and coordination moiety. There is a linear geometry (containing Ipr and dimethyl thiocarbamate ligand molecules) around central gold atoms in each molecule. Dimethyl thiocarbamate is acting as a coordinated counter anion in this complex molecule. The central gold(I) atom is coordinated with one C donor atom of the Ipr ligand molecule and S atom of (S$_2$CNMe$_2$)$^-$ counter anion. The Au atom adopts a most familiar linear C—Au—S coordination geometry like gold (I) complexes (FIG. 2).

The Au—S and Au—C bond average distances are 2.30 (17) and 2.00 (6) Å respectively. The C—Au—S average bond angle 175.22 (2)°. The bond angle around Au(I) atom show considerable deviation from the ideal linear angle value 180° (Tables 4 and 5).

TABLE 4

Crystallographic characteristics, experimental and structure refinement details for crystal structure of complex complexes (1-3).

| Parameters | Complex 1 | Complex 2 | Complex 3 |
|---|---|---|---|
| Empirical formula | C$_{30}$H$_{42}$AuN$_3$S$_2$ | C$_{32}$H$_{45}$AuN$_3$S$_2$ | C$_{42}$H$_{50}$AuN$_3$S$_2$ |
| Empirical formula weight | 705.75 | 733.8 | 857.94 |
| Crystal size/mm | 0.45 × 0.30 × 0.20 | 0.45 × 0.38 × 0.30 | 0.45 × 0.42 × 0.35 |
| Wavelength/Å | 0.71073 | 0.71073 | 0.71073 |
| Temperature/K | 173 | 173 | 173 |
| Crystal symmetry | Monoclinic | Orthorhombic | Orthorhombic |
| Space group | P2$_1$/c | Pna2$_1$ | Pna2$_1$ |
| a/Å | 13.2323 (4) | 42.4867 (11) | 25.7815 (9) |
| b/Å | 28.9995 (11) | 16.4047 (5) | 12.4955 (4) |
| c/Å | 17.1760 (5) | 19.1873 (5) | 12.0577 (5) |
| β/° | 104.687 (2)° | | |
| V/Å$^3$ | 6375.6 (4) | 4416.3 (5) | 3884.4 (2) |
| Z | 8 | 16 | 4 |
| D$_c$/Mg m$^{-3}$ | 1.471 | 1.458 | 1.467 |
| µ(Mo-Kα)/mm$^{-1}$ | 4.77 | 4.55 | 3.93 |
| F(000) | 2832 | 5920 | 1736 |
| θ Limits/° | 1.4-26.1 | 1.2-26.2 | 1.6-26.1 |
| Collected reflections | 83,383 | 98,752 | 25,927 |
| Unique reflections | 8469 | 15,664 | 6167 |
| Observed reflections | 11,547 | 23,566 | 7312 |
| Goodness of fit on F$^2$ | 1 | 0.94 | 1 |
| R$_1$ [F$^2$ > 2σ(F$^2$)] | 0.048 | 0.052 | 0.029 |
| wR$_2$ (F$^2$) | 0.081 | 0.095 | 0.06 |
| Largest diff. peak, hole/e Å$^{-3}$ | 3.19, −0.96 | 1.07, −1.30 | 1.24, −2.05 |

TABLE 5

Selected bond distances (Å) and bond angles (°) for complexes (1-3).

| Complex 1 Bond length (Å) | | Complex 2 Bond length (Å) | | Complex 3 Bond length (Å) | |
|---|---|---|---|---|---|
| Au1—S1 | 2.3062 (17) | Au1—C6 | 2.02 (2) | Au1—C16 | 2.001 (5) |
| Au2—S3 | 2.2985 (17) | Au1—S1 | 2.314 (5) | Au1—S1 | 2.2999 (12) |
| Au1—C4 | 2.011 (7) | Au2—C38 | 1.984 (17) | | |
| Au2—C34 | 1.998 (6) | Au2—S3 | 2.301 (5) | | |
| | | Au3—C70 | 1.994 (19) | | |
| | | Au3—S5 | 2.310 (5) | | |
| | | Au4—C102 | 2.05 (2) | | |
| | | Au4—S7 | 2.307 (5) | | |

| Bond angles (°) | | Bond angles (°) | | Bond angles (°) | |
|---|---|---|---|---|---|
| C4—Au1—S1 | 175.38 (19) | C6—Au1—S | 1171.2 (5) | C16—Au1—S1 | 170.76 (13) |
| C1—S1—Au1 | 99.7 (2) | C1—S1—Au1 | 101.0 (7) | C1—S1—Au1 | 105.3 (2) |
| C34—Au2—S3 | 175.07 (19) | C38—Au2—S3 | 173.7 (6) | | |
| C31—S3—Au2 | 103.3 (2) | C33—S3—Au2 | 103.1 (7) | | |
| | | C70—Au3—S5 | 173.9 (6) | | |
| | | C65—S5—Au3 | 103.0 (6) | | |
| | | C102—Au4—S7 | 172.2 (5) | | |
| | | C97—S7—Au4 | 104.7 (7) | | |

The Au—S bond distances are different to those found in a literature complex, see S. Y. Ho, E. R. T. Tiekink, Z. Krist. 220 (2005) 342-344, incorporated herein by reference in its entirety. Similarly, the S—Au—C bond angle is also considerably different from those found in [Et$_3$PAu(S$_2$CNEt$_2$)] complex and other mononuclear [(t-Bu)PAu]$^+$ complexes with linear geometry with gold central atom [S. Y. Ho, E. R. T. Tiekink, Z. Krist. 220 (2005) 342-344; I. Sänger, H.-W. Lerner, T. Sinke, M. Bolte, Acta Crystallogr. E68 (2012) m708; P. Lu, T. C. Boorman, A. M. Z. Slawin, I. Larrosa, J. Am. Chem. Soc. 132 (2010) 5580-5581; R. E. Marsh, Acta Crystallogr. B58 (2002) 893-899; H. Schmidbaur, B. Brachthiuser, O. Steigelmann, H. Beruda, Chem. Ber. 125 (1992) 2705-2710; E. Barreiro, J. S. Casas, M. D. Couce, A. Sánchez, J. Sordo, E. M. Vázquez-López, J. Inorg. Biochem. 131 (2014) 68-75; and R. Kivekäs, E. Colacio, J. Ruiz, J. D. López-González, P. León, Inorg. Chim. Acta 159 (1989) 103-110—each incorporated herein by reference in their entirety]. This variation in bond angle is attributed to the presence of different coordination environment in the reported complexes.

Crystal Structure of Complex [Au(Ipr)(S$_2$CN(C$_2$H$_2$)$_2$)] (2)

Figure 3A:
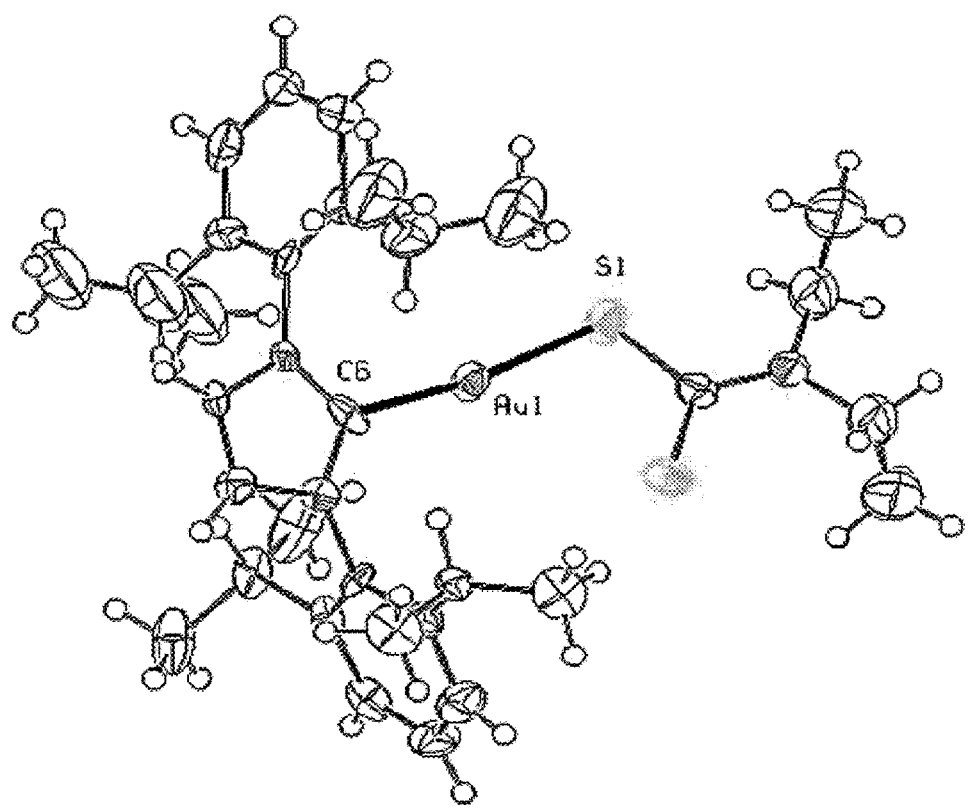
FIG. 3A is a view of the molecular structure of mononuclear complex 2 [(Ipr)Au(S$_2$CN(C$_2$H$_5$)$_2$)], with atom labeling scheme and displacement ellipsoids drawn at 50% probability level (three molecules have been omitted for clarity).
Figure 3B:
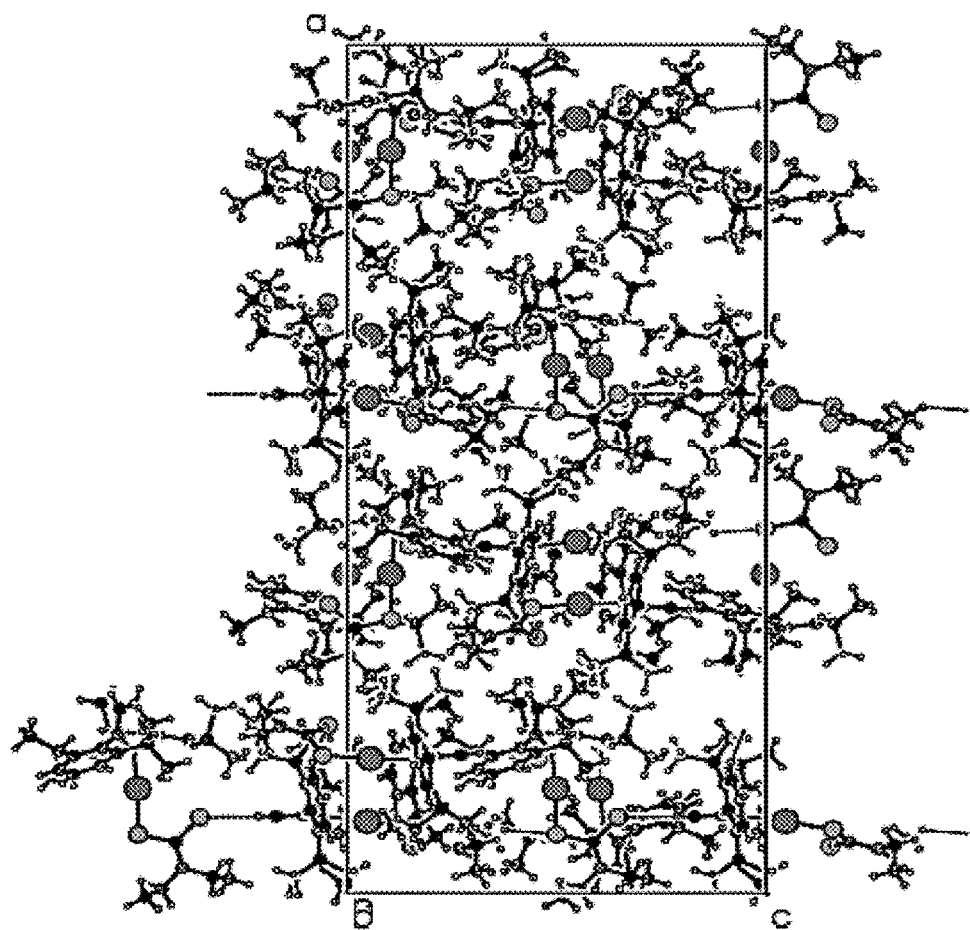
FIG. 3B is a packing diagram along b axis of complex 2, showing a hydrogen bonding network.

There four virtually identical molecules in the asymmetric unit of x-ray structure of gold(I) complex 2 (FIG. 1C) containing the same Ipr ligand molecule and [(S$_2$CNEt$_2$)]$^-$ counter ion as shown in FIGS. 3A and 3B. In all molecules, gold(I) is coordinated with one C donor atom of Ipr ligand molecule and one S donor atom of the [(S$_2$CNEt$_2$)]$^-$ ligand molecule.

The Au—S bond distances are almost same and around 2.31 (5) Å in all four molecules. The Au—C bond distances are also similar and around 2.00 (2) Å, which is close to double bond. The Au—S bond distances are very much similar to [Au(Ipr)(S$_2$CN(CH$_3$)$_2$)] (1) complex and comparable with [Et$_3$PAu(S$_2$CNEt$_2$)] complex. The Au—C bond distance is almost identical as found in complex (1).

The geometry around Au(I) metal atom is conventionally linear and similar to each other and complex (1). In this structure S—Au—C bond angles are around 172.00 (2)°. There is a big distortion from ideal linearity in each molecule as seen in complex (1). These bond angle values around central gold atom in all four molecules confirm the presence of pseudo distorted linear geometry around gold(I) atoms in this structure. These bond angle values also show big deviation from ideal linear angle of 180° (Table 5). The overall geometry of [Au(Ipr)(S$_2$CN(C$_2$H$_5$)$_2$)] (2) closely resembles those Au(I) complexes.

Crystal Structure of Complex [Au(Ipr)(S$_2$CN(C$_7$H$_7$)$_2$)] (3)

Figure 1D:
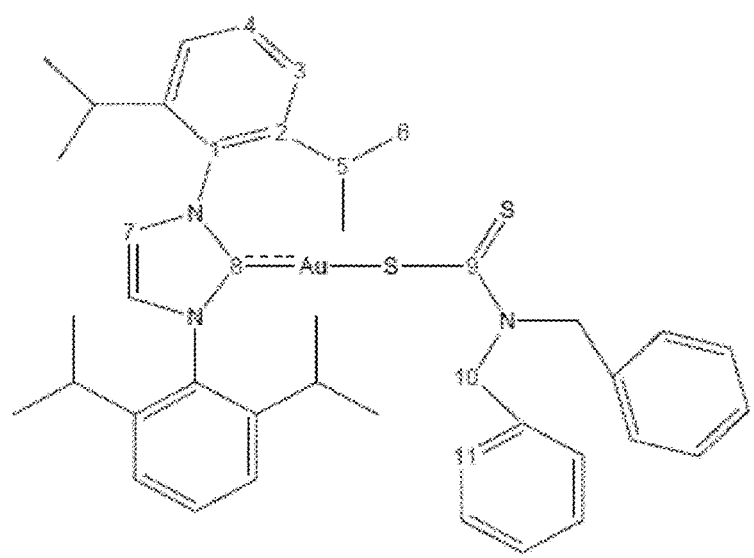
FIG. 1D is a skeletal structure of complex 3 [(Ipr)Au(S$_2$CN(C$_7$H$_7$)$_2$)]
Figure 4:
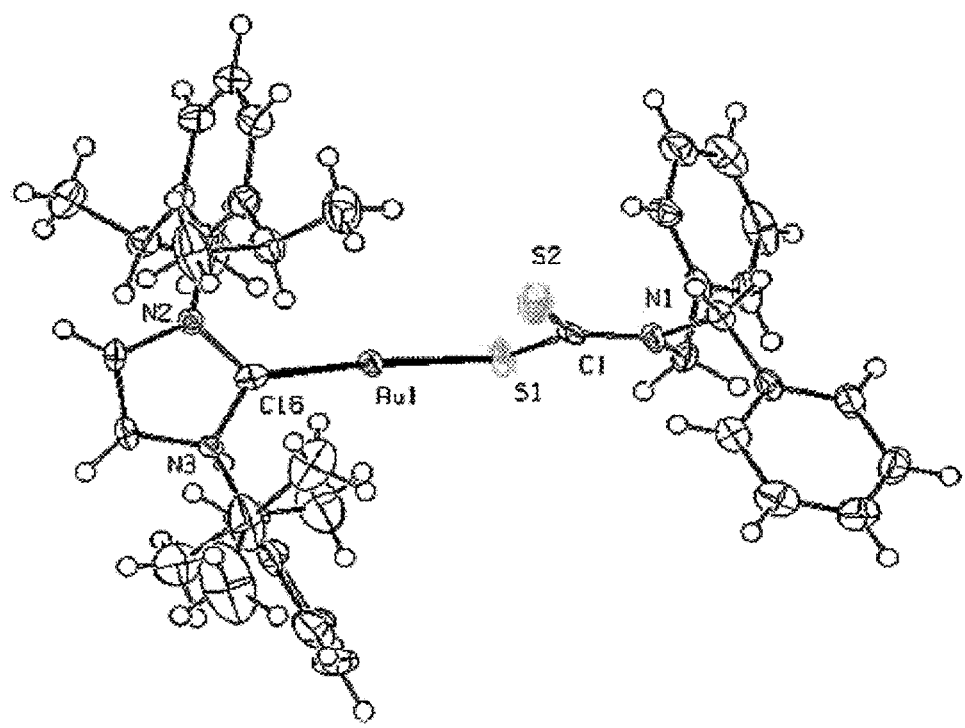
FIG. 4 is a view of the molecular structure of mononuclear complex 3 [(Ipr)Au(S$_2$CN(C$_7$H$_7$)$_2$)], with atom labeling scheme and displacement ellipsoids drawn at 50% probability level.
Figure 5:
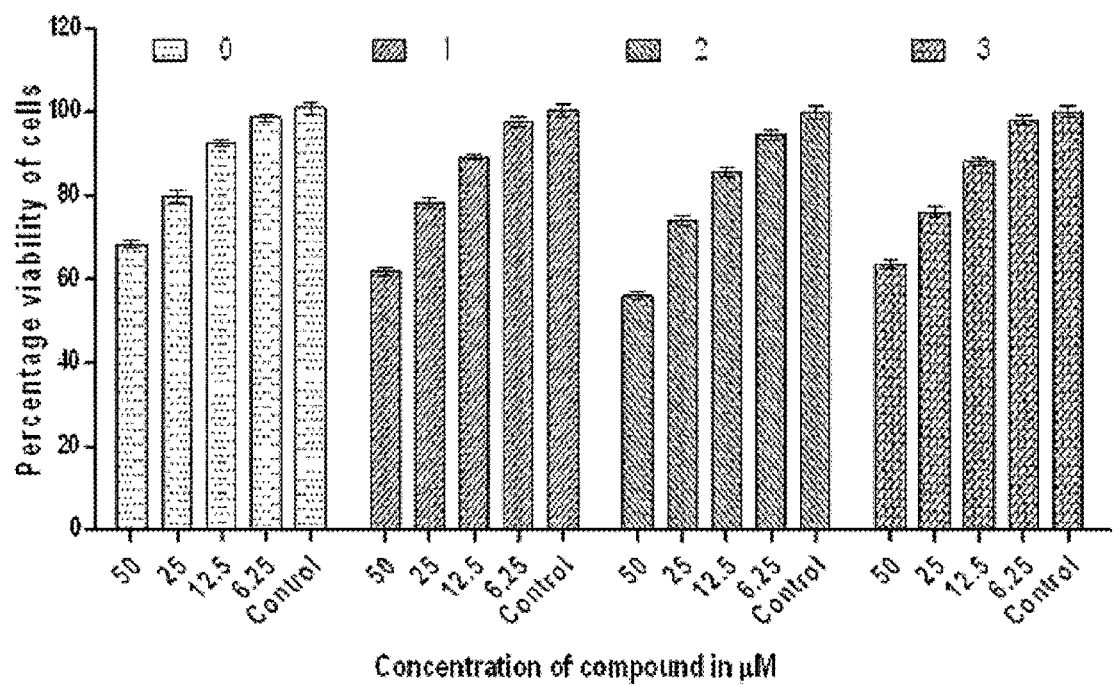
FIG. 5 is a graph showing the cytotoxic effect of series of concentrations of compounds 0-3 on viability of HeLa cells.
Figure 6:
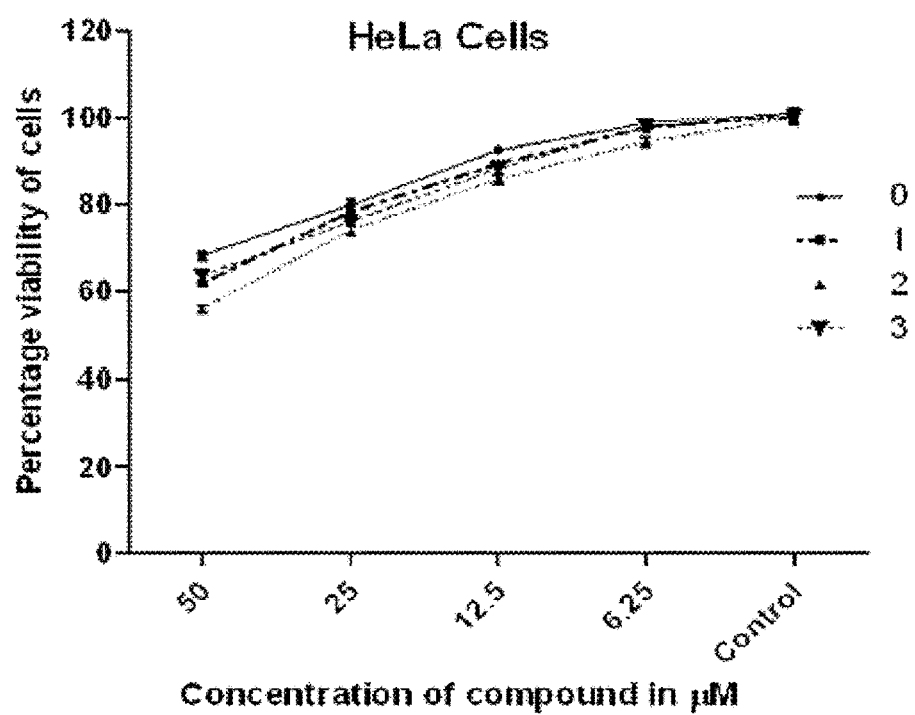
FIG. 6 is a graph of in vitro cytotoxic effect of series of concentrations of compounds 0-3 on a HeLa cell line.
Figure 7:
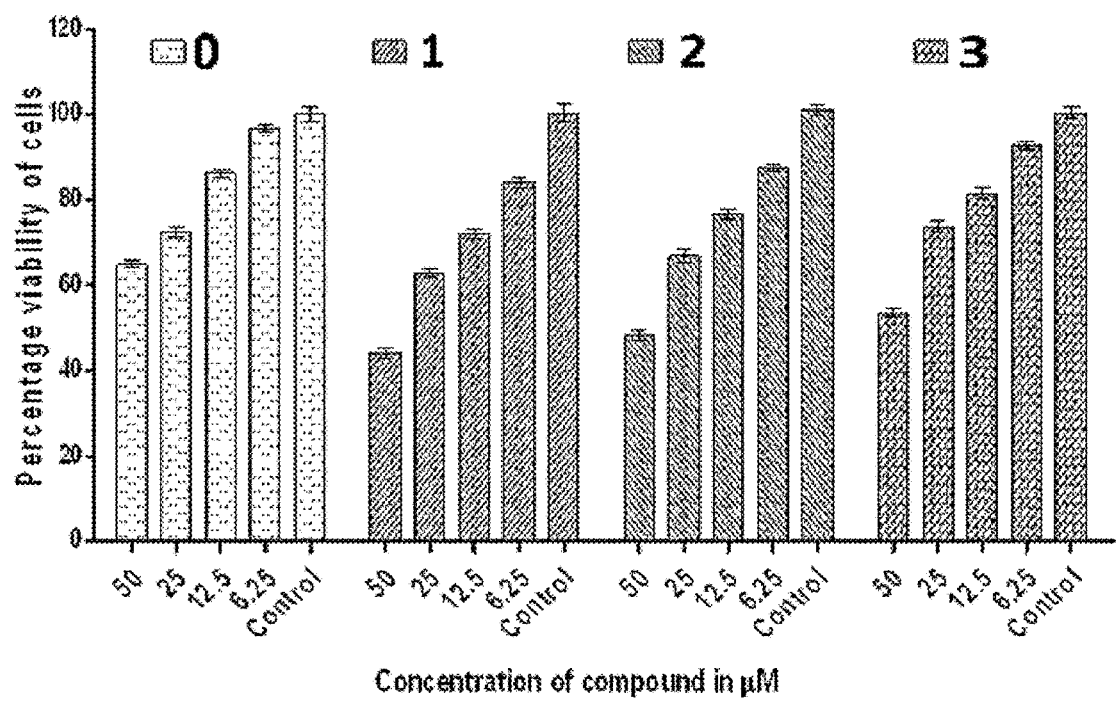
FIG. 7 is a graph showing the cytotoxic effect of series of concentrations of compounds 0-3 on viability of HCT15 cells.
Figure 8:
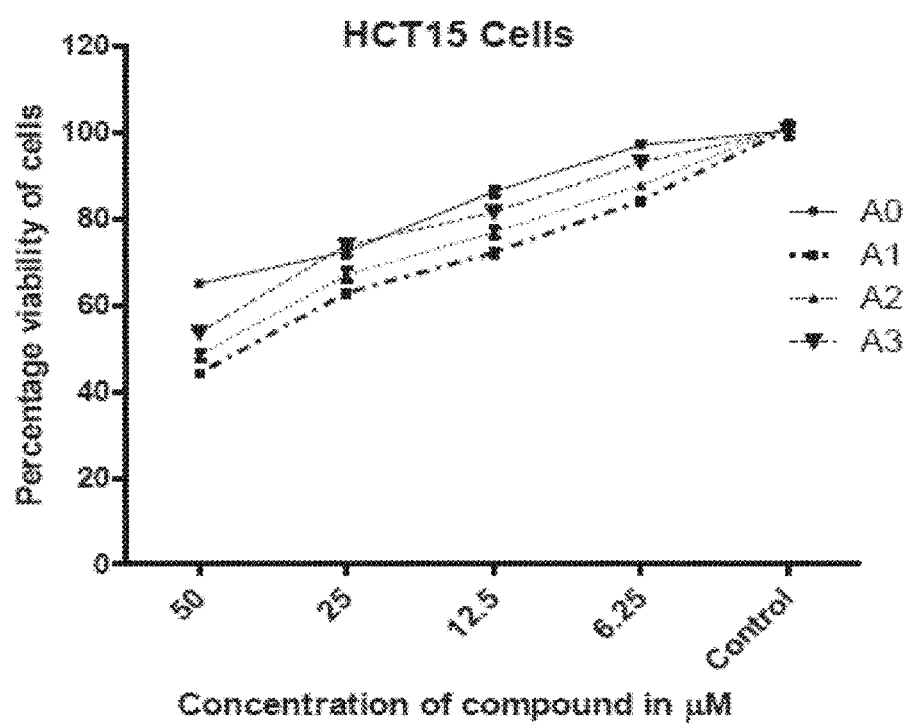
FIG. 8 is a graph showing the cytotoxic effect of series of concentrations of compounds 0-3 on a HCT15 cell line.
Figure 9:
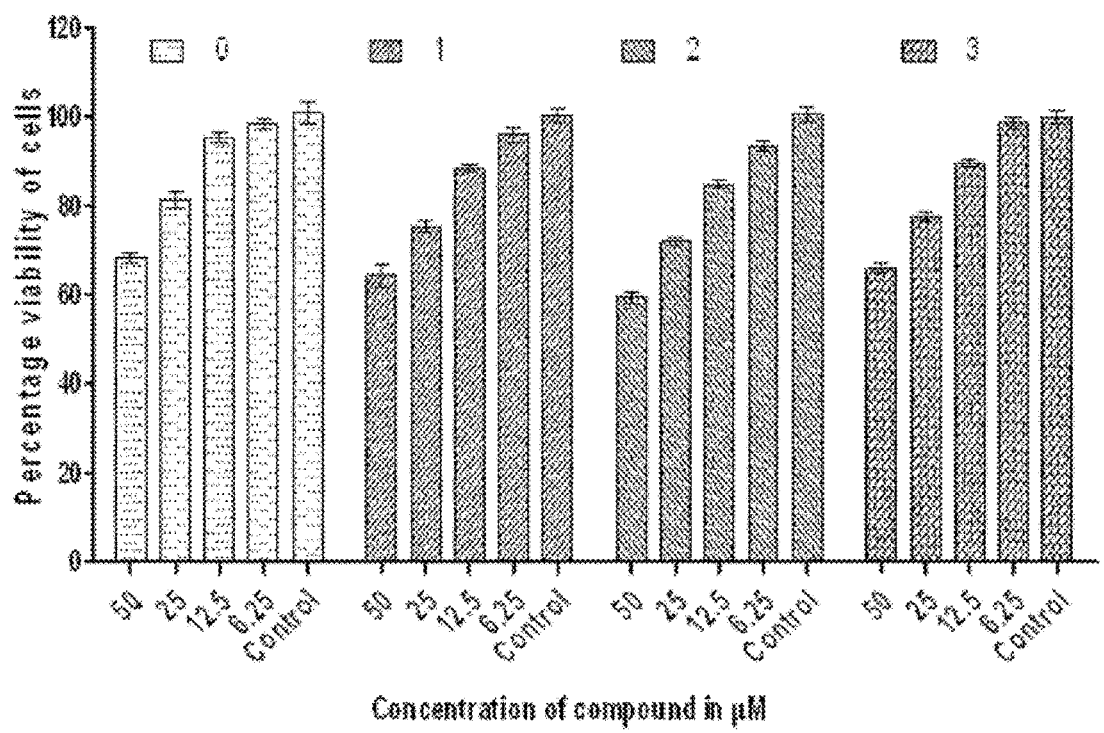
FIG. 9 is a graph showing the cytotoxic effect of series of concentrations of compounds 0-3 on viability of A549 cells.
Figure 10:
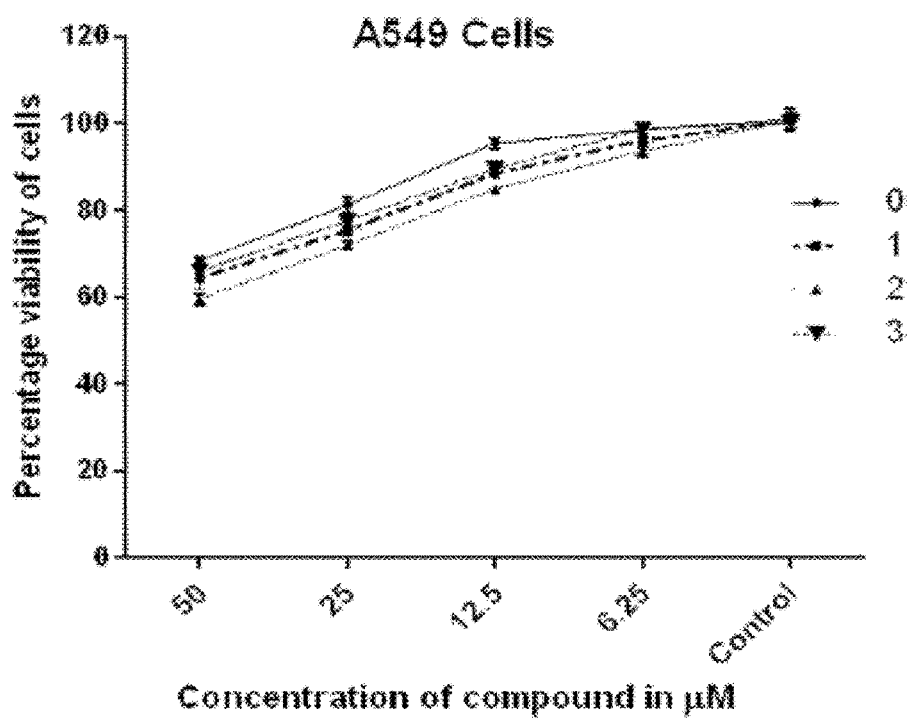
FIG. 10 is a graph showing the cytotoxic effect of series of concentrations of compounds 0-3 on a A549 cell line.

Molecular structure of [Au(Ipr)(S$_2$CN(C$_7$H$_7$)$_2$)] (3) is shown in FIG. 1D. In this structure gold(I) is coordinated with one C donor atom and one S donor atom of two different type ligands (FIG. 4).

The Au—S and Au—C bond distances are 2.2999 (12) and 2.001 (5) Å respectively. The Au—C and Au—S bond distances are similar to complexes (1) and (2) and comparable with [Et$_3$PAu(S$_2$CNEt$_2$)] complex. The geometry around Au(I) metal atom is linear and similar to complexes (1 and 2) and other Au(I) complexes. In the [Au(Ipr)(S$_2$CN(C$_7$H$_7$)$_2$)] (3) structure, the S—Au—C bond angle is 170.76 (13)°. The bond angle value around central gold atom in this molecule confirms the presence of pseudo distorted linear geometry around gold(I) atom. This bond angle value is considerably different than complexes (1 and 2). This bond angle value also shows big deviation from ideal linear angle of 180° (Table 5).

Example 3

In Vitro Cytotoxic Effects of Complexes (1), (2) and (3)

The in vitro cytotoxicity tests were carried out for the gold(I) precursor, labeled as complex 0 and the three synthesized complexes labeled as complex 1, 2 and 3 and compared with cisplatin (standard classical anticancer drug) against three human cancer cell lines, HCT15, HeLa and A549 using MTT assay. The dose dependent cytotoxic effect was obtained by the stipulated increase in concentrations of cisplatin and gold complexes 0-3 against the fixed number of human cancer cells. The IC$_{50}$ concentration of cisplatin and complexes 0-3 for different human cancer cell lines was obtained from a curve between compound concentration and percentage viability of cells (FIGS. 5-10, Table 6).

TABLE 6

IC$_{50}$ values (µM) of gold(I) complexes against
A549, HeLa and HCT15 cancer cell lines.

| Complex | A549 | HeLa | HCT15 |
|---|---|---|---|
| Cisplatin | 41.6 | 19.4 | 29.5 |
| (0) | 180.2 | 172.5 | 121.7 |
| (1) | 133.9 | 108.3 | 41.1 |
| (2) | 91.7 | 79.6 | 24.5 |
| (3) | 139.9 | 124.6 | 27.4 |

Figure 11:
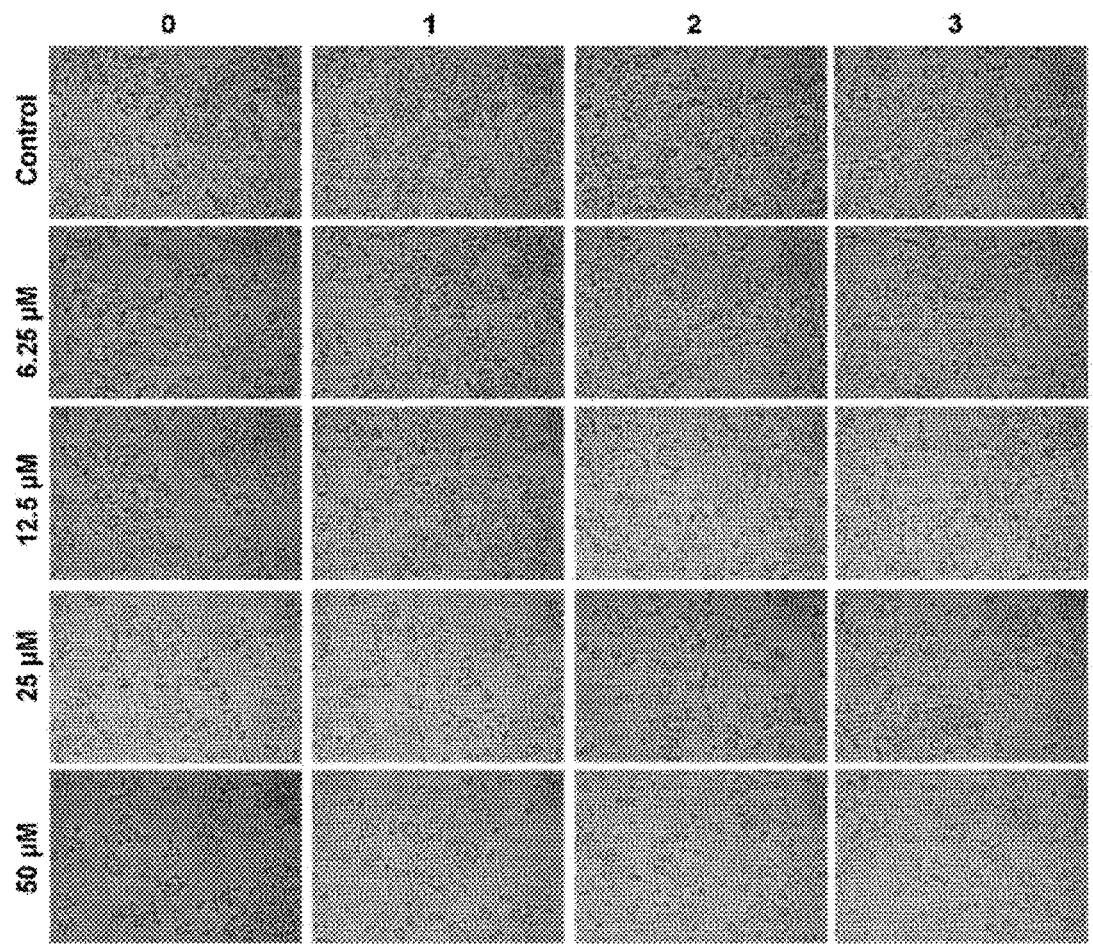
FIG. 11 is an illustration of morphological changes in HCT15 cells treated with series of concentrations of compounds 0-3 studied using phase contrast microscopy.
Figure 12:
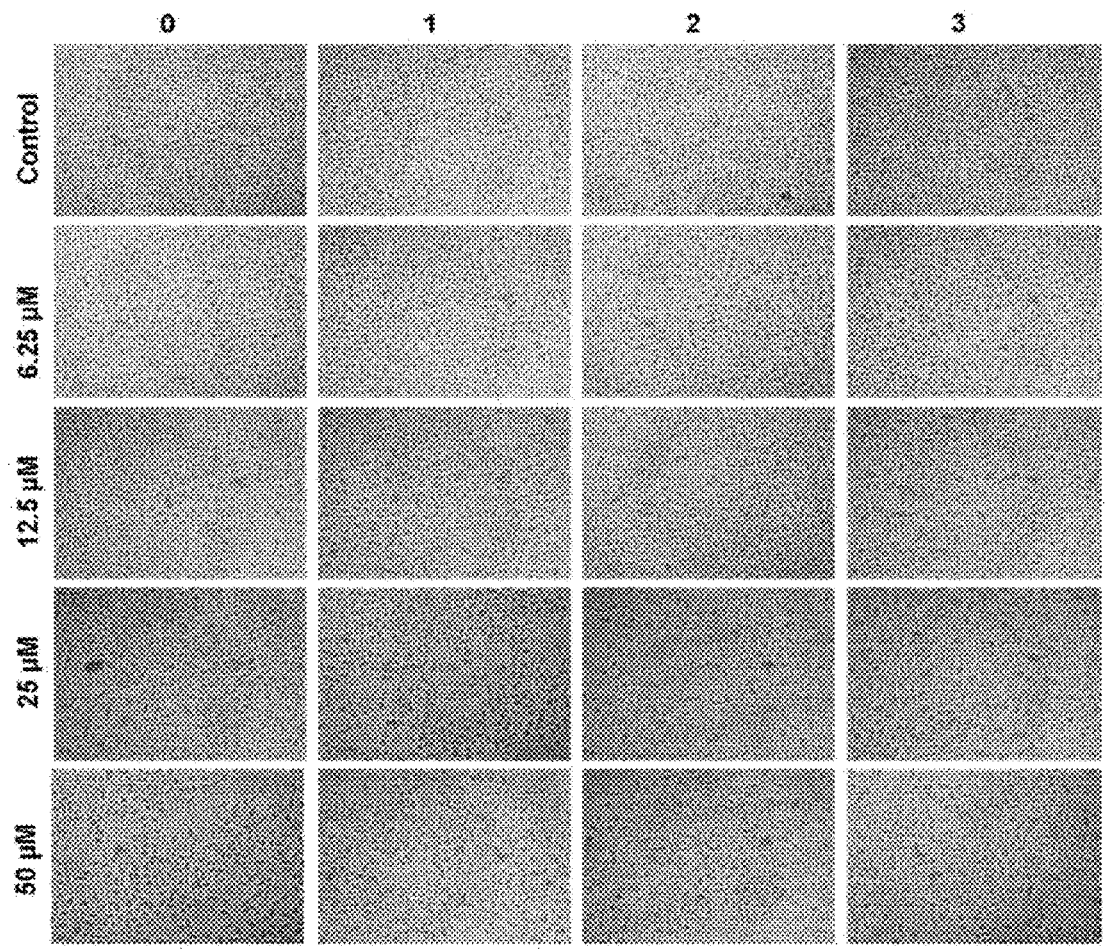
FIG. 12 is an illustration of morphological changes in A549 cells treated with series of concentrations of compounds 0-3 studied using phase contrast microscopy.
Figure 13:
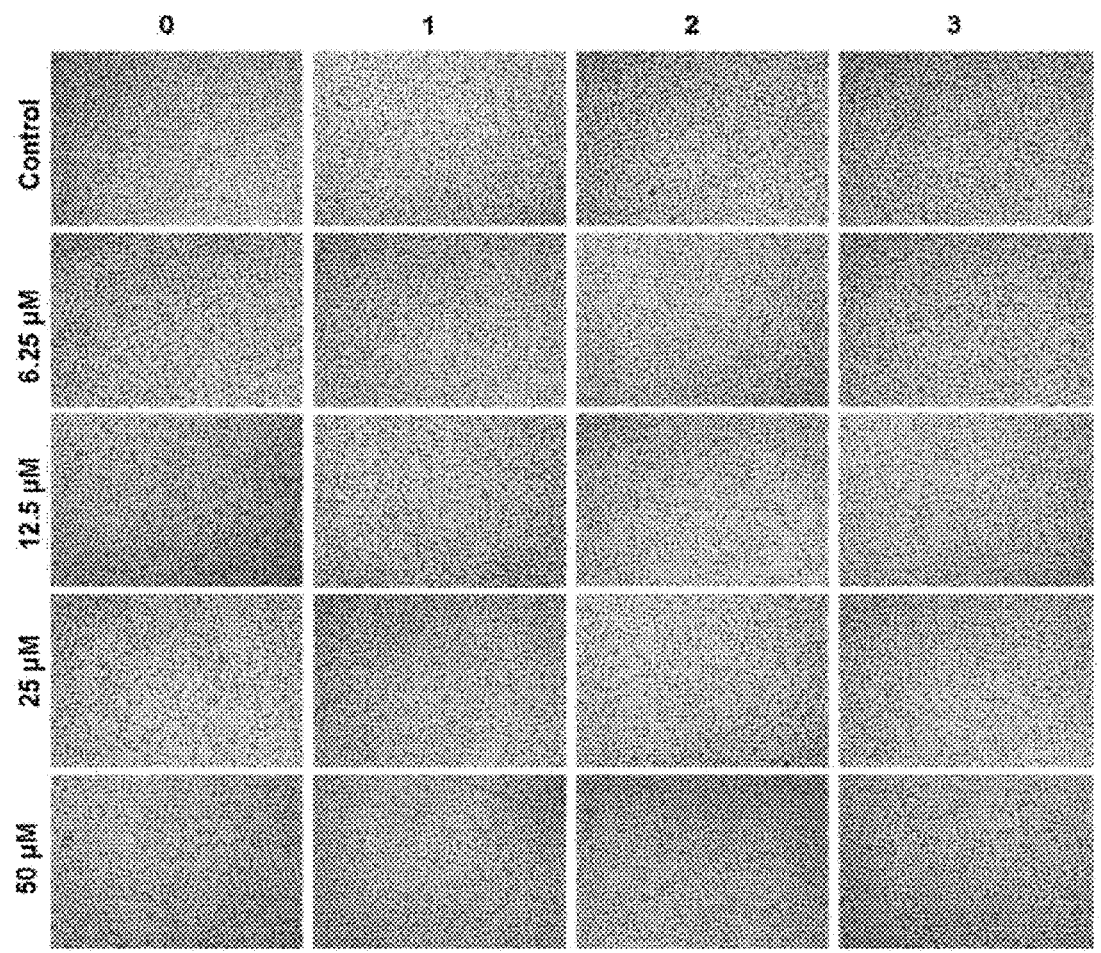
FIG. 13 is an illustration of morphological changes in HeLa cells treated with series of concentrations of compounds 0-3 studied using phase contrast microscopy.

In phase contrast micrographs, a decreasing cell density and deformed cellular morphology could be observed with increasing concentration of complexes 0-3 (FIGS. 11-13). The dose dependent decrease in cell density was further supported by assessment of decreasing percent cell viability in MTT assay (FIGS. 5-10). The IC$_{50}$ concentrations of gold complexes were calculated from a separate curve between complex concentration and % viability of cells plotted in Microsoft Excel 2007 (graphs not shown) using MTT assay data and explained by logarithmic regression equations (equations not shown).

All the synthesized complexes 1-3 exhibit moderate anticancer activity ranging between 24.5 and 180.2 µM in accordance to the previous reports on anticancer studies of gold complexes. These complexes showed better anti-cancer activity than free gold(I) precursor 0, which could be attributed to dithiocarbamate ligands bonded to central gold(I) ion. Dithiocarbamate ligands may be better leaving groups than chloride ions and facilitate the availability of gold atom to interact with cancer cells to inhibit their growth in vitro. The IC$_{50}$ values of complexes 1-3 against A549 and HeLa cell lines were higher than classical anticancer drug, cisplatin. The IC$_{50}$ values against HCT15 cell line of synthesized complexes (2 and 3) show moderate potency but better than cisplatin [L. Ortego, F. Cardoso, S. Martins, M. F. Fillat, A. Laguna, M. Meireles, M. D. Villacampa, M. C. Gimeno, J. Inorg. Biochem. 130 (2014) 32-37 and I. Ott, T. Koch, H. Shorafa, Z. Bai, D. Poeckel, D. Steinhilber, R. Gust, Org. Biomol. Chem. 3 (2005) 2282-2286—each incorporated herein by reference in their entirety].

Gold complexes are well known for their broad spectrum of therapeutic and cytotoxic activity against pathogen agents, together with their lack of cross-resistance with antibiotics. The X-ray structures of all three complexes (1, 2 and 3) with CAuS moiety have nearly linear geometry which is a typical feature for gold(I) complexes.

The high IC$_{50}$ values against all three cancer cell lines are due to strong Au—C bond and bulky carbene ligand. These factors slow down the dissociation of gold complex and its interaction with cancer cells. According to our observation, this is the major factor for slow inhibition of growth of cancer cell lines for all (1, 2 and 3) complexes. The in vitro cytotoxicity of gold complexes (2 and 3) was quite promising and better than cisplatin. All the three complexes show good selectivity of inhibition of growth of a HCT15 cancer line.

Example 4

Experimental

Materials and Methods

All the reactions were carried under normal ambient conditions. All chemical and solvents used in the synthesis were of analytical grade and were used without further purification. All chemicals were purchased from Sigma-Aldrich St. Louis, Mo. United States and Strem Chemicals, Massachusetts, United States.

Elemental analyses were performed on Perkin Elmer Series 11 (CHNS/O), Analyzer 2400. The solid state FTIR spectra of the ligands and their gold(I) complexes were recorded on a Perkin-Elmer FTIR 180 spectrophotometer or NICOLET 6700 FTIR using KBr pellets over the range 4000-400 cm$^{-1}$.

$^1$H and $^{13}$C NMR spectra were recorded on a LAMBDA 500 spectrophotometer operating at 500.01, 125.65 and 200.0 MHz respectively; corresponding to a magnetic field of 11.74 T. Tetra-methylsilane (TMS) was used as an internal standard for $^1$H and $^{13}$C NMR measurements. The $^{13}$C NMR spectra were obtained with $^1$H broadband decoupling, and the spectral conditions were: 32 k data points, 0.967 s acquisition time, and 1.00 s pulse delay and 45° pulse angle. The $^1$H and $^{13}$C NMR chemical shifts are given in Tables 2 and 3 respectively.

Example 5

Syntheses of Gold(I) Complexes

Synthesis of [Au(Ipr)(S$_2$CN(CH$_3$)$_2$)] (1)

1,3-Bis(2,6-di-isopropylphenyl)imidazol-2-ylidenegold (I)chloride, [(Ipr)Au(Cl)] (0.311 g, 0.05 mmol) in 10 mL ethanol was added drop wise to an ethanolic solution of sodium dimethyldithio-carbamate monohydrate (0.072 g, 0.05 mmol) at room temperature with continuous stirring for 3 h. Subsequently 1-3 mL of water was added to the reaction mixture to get the clear solution. The clear yellow solution obtained was filtered to avoid any impurity and kept undisturbed for crystallization by slow evaporation at room temperature. After five days yellow block like crystals were obtained. A well-shaped good quality crystal was chosen for X-ray diffraction analysis. Anal. Calc. for C$_{30}$H$_{42}$AuN$_3$S$_2$: C, 51.05; H, 6.00; N, 5.95; S, 9.07. found: C, 51.80; H, 6.33; N, 5.87; S, 8.98. Yield: 0.314 g, (89%).

Synthesis of [Au(Ipr)(S$_2$CN(C$_2$H$_5$)$_2$)] (2)

This complex was synthesized with sodium diethyldithiocarbamatetrihydrate (0.113 g, 0.05 mmol) by a procedure analogous to (1). After eight days colorless block like crystals were obtained. A suitable quality crystal was chosen for X-ray diffraction analysis. Anal. Calc. for C$_{32}$H$_{46}$AuN$_3$S$_2$: C, 52.38; H, 6.31; N, 5.72; S, 8.74. found: C, 52.19; H, 6.37; N, 5.70; S, 8.68. Yield: 0.337 g, (92%).

Synthesis of [Au(Ipr)(S$_2$CN(C$_7$H$_7$)$_2$)] (3)

This complex was synthesized with sodium diebenzyldithiocarbamatetrihydrate (0.136 g, 0.05 mmol) by a procedure adopted for (1). After seven days colorless block like crystals were obtained. A well-shaped bright, crystal was chosen for X-ray diffraction analysis. Anal. Calc. for C$_{42}$H$_{54}$AuN$_2$S$_2$: C, 58.52; H, 6.31; N, 4.87; S, 7.44. found: C, 58.19; H, 6.38; N, 4.78; S, 7.57. Yield: 0.357 g, (83%).

Example 6

X-Ray Structure Determination

For gold(I) complexes 1-3, quality single were obtained from a solution of C$_2$H$_5$OH and H$_2$O. The intensity data were collected at 173 K on a two circle (χ and u scans) Stoe Image Plate Diffraction System, using Mo Kα graphite monochromated radiation [G. M. Sheldrick, Acta Crystallogr. A64 (2008) 112-122—incorporated herein by reference in its entirety]. The structures were solved by direct methods, using the program SHELXS-97. The refinement and all further calculations were carried out using SHELXL-97. The H-atoms were either located from Fourier difference maps and freely refined or included in calculated positions and treated as riding atoms using SHELXL default parameters. The non-H atoms were refined anisotropically, using weighted full-matrix least-squares on $F^2$. Empirical or multiscan absorption corrections were applied using the MULSCANABS routines in PLATON [A. L. Spek, Acta Crystallogr. D65 (2009) 148-155—incorporated herein by reference in its entirety]. FIGS. 2-4 were drawn using the programs ORTEP and MERCURY [C. F. Macrae, P. R. Edgington, P. McCabe, E. Pidcock, G. P. Shields, R. Taylor, M. Towler, J. van de Streek, J. Appl. Crystallogr. 39 (2006) 453-457—incorporated herein by reference in its entirety]. A summary of crystal data and refinement details for gold(I) complexes 1-3 are given in Table 4. Selected bond lengths and bond angles are given in Table 5.

Example 7

In Vitro Cytotoxic Activity Against A549, HCT15 and HeLa Human Cancer Cell Lines The metal precursor (complex 0) and the three synthesized compounds 1-3 were evaluated for their in vitro cytotoxic activity against HCT15 (human cancer), HeLa (human cervical cancer) and A549 (human lung carcinoma) cell lines. The cells were seeded at $4 \times 10^3$ cells/well in 100 μL DMEM (Dulbecco's Modified Eagle's Medium) containing 10%. FBS (Fetal Bovine Serum) in 96-wells tissue culture plate and incubated for 72 h at 37° C., 5% $CO_2$ in air and 90% relative humidity in $CO_2$ incubator. After incubation, 100 μL of 50, 25, 12.5 and 6.25 μg/mL solutions of complexes (0-3), prepared in DMEM, were added to cells and the cultures were incubated for 24 h. The medium of wells was discarded and 100 μL DMEM containing MTT (3-(4,5-dimethylthiazol-2-yl)-2,5-diphenyltetrazolium bromide) (5 mg/mL) was added to the wells and incubated in $CO_2$ incubator at 37° C. in dark for 4 h. After incubation, a purple colored formazan (artificial chromogenic dye, product of the reduction of water insoluble tetrazolium salts e.g., MMT by dehydrogenases and reductases) in the cells is produced and appeared as dark crystals in the bottom of the wells. The medium of culture was discarded from each well carefully to avoid disruption of monolayer and 100 μl of dimethyl sulfoxide (DMSO) was added in each well. The solution was thoroughly mixed in the wells to dissolve the formazan crystals which ultimately result into a purple solution. The absorbance of the 96-wells plate was taken at 570 nm with Labsystems Multiskan EX-Enzyme-linked immunosorbent assay (EX-ELISA) reader against a reagent blank.

The invention claimed is:

1. A N-heterocyclic carbene-gold(I) dithiocarbamate complex of formula I

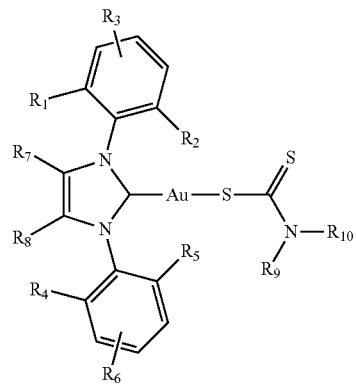

or a pharmaceutically acceptable salt, solvate, or prodrug thereof
wherein:
$R_1$, $R_2$, $R_3$, $R_4$, $R_5$, $R_6$, $R_7$, $R_8$ are each independently a hydrogen, an optionally substituted alkyl, an optionally substituted cycloalkyl, an optionally substituted heterocyclyl, an optionally substituted arylalkyl, an optionally substituted heteroaryl, an optionally substituted alkoxyl, an optionally substituted thioalkoxyl, an optionally substituted aryl, a N-monosubstituted amino group, or a N,N-disubstituted amino group; and
$R_9$ and $R_{10}$ are each independently a hydrogen, an optionally substituted $C_1$-$C_8$ alkyl, an optionally substituted cycloalkyl, an optionally substituted heterocyclyl, an optionally substituted arylalkyl, an optionally substituted heteroaryl, an optionally substituted alkoxyl, an optionally substituted aryl, a N-monosubstituted amino group, or a N,N-disubstituted amino group;
wherein the $C_1$-$C_8$ alkyl is optionally substituted with at least one substituent selected from the group consisting of hydroxyl, amino, alkylamino, arylamino, alkoxy, aryloxy, halo nitro, cyano, sulfonic acid, sulfate phosphonic acid, phosphate and phosphonate.

2. The N-heterocyclic carbene-gold(I) dithiocarbamate complex of formula I of claim 1, wherein:
$R_1$, $R_2$, $R_4$, and $R_5$ are each methyl, ethyl, isopropyl or t-butyl;
$R_3$, $R_6$, $R_7$, and $R_8$ are hydrogen; and
$R_9$ and $R_{10}$ are each methyl, ethyl, isopropyl, benzyl, or phenyl.

3. The N-heterocyclic carbene-gold(I) dithiocarbamate complex of formula I of claim 1, which is

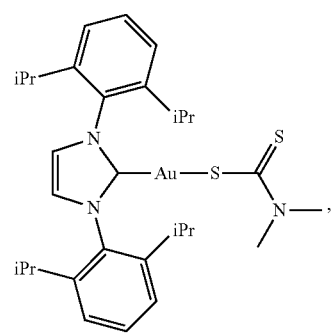

-continued

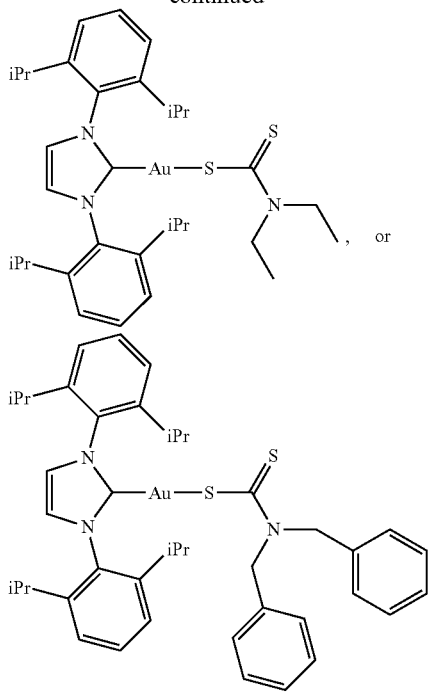

4. The N-heterocyclic carbene-gold(I) dithiocarbamate complex of formula I of claim 1, wherein the complex has in vitro cytotoxic activity against A549, HeLa, HCT15 and cancer cell lines with an $IC_{50}$ value of that does not exceed 160 μM.

5. A pharmaceutical composition, comprising
the N-heterocyclic carbene-gold(I) dithiocarbamate complex of formula I of claim 1 or a pharmaceutically acceptable salt, solvate, or prodrug thereof and
a pharmaceutically acceptable carrier or excipient.

6. The pharmaceutical composition of claim 5, further comprising one or more other active pharmaceutical agents.

7. The pharmaceutical composition of claim 5, wherein the composition is in solid, semi-solid or liquid dosage forms.

8. The pharmaceutical composition of claim 5, wherein the composition is formulated for at least one mode of administration selected from the group consisting of oral administration, systemic administration, parenteral administration, inhalation spray, infusion, rectal administration, topical administration, intravesical administration, intradermal administration, transdermal administration, subcutaneous administration, intramuscular administration, intralesional administration, intracranial administration, intrapulmonal administration, intracardial administration, intrasternal administration and sublingual administration.

9. A method for the treatment of lung, cervix, and/or colon cancer in a patient, comprising
administering to the patient a therapeutically effective amount of the N-heterocyclic carbene-gold(I) dithiocarbamate complex of formula I of claim 1 or a pharmaceutically acceptable salt, solvate, or prodrug thereof.

10. The method of claim 9, wherein the N-heterocyclic carbene-gold(I) dithiocarbamate complex exhibits an $IC_{50}$ value that does not exceed 160 μM against lung, cervix, or colon cancer.

11. The method of claim 9, wherein the administering is by oral administration, systemic administration, parenteral administration, inhalation spray, infusion, rectal administration, topical administration, intravesical administration, intradermal administration, transdermal administration, subcutaneous administration, intramuscular administration, intralesional administration, intracranial administration, intrapulmonal administration, intracardial administration, intrasternal administration, or sublingual administration.

* * * * *